(12) United States Patent
Gavathiotis et al.

(10) Patent No.: US 11,174,308 B2
(45) Date of Patent: Nov. 16, 2021

(54) SYNTHETIC ANTIBODIES TO BAX AND USES THEREOF

(71) Applicants: ALBERT EINSTEIN COLLEGE OF MEDICINE, Bronx, NY (US); THE GOVERNING COUNCIL OF THE UNIVERSITY OF TORONTO, Toronto (CA)

(72) Inventors: Evripidis Gavathiotis, Flushing, NY (US); Jonathan R. Lai, Dobbs Ferry, NY (US); Sachdev Sidhu, Toronto (CA)

(73) Assignees: ALBERT EINSTEIN COLLEGE OF MEDICINE, INC., Bronx, NY (US); THE GOVERNING COUNCIL OF THE UNIVERSITY OF TORONTO, Toronto (CA)

(*) Notice: Subject to any disclaimer, the term of this patent is extended or adjusted under 35 U.S.C. 154(b) by 0 days.

(21) Appl. No.: 16/988,947

(22) Filed: Aug. 10, 2020

(65) Prior Publication Data

US 2020/0399356 A1    Dec. 24, 2020

Related U.S. Application Data

(62) Division of application No. 16/261,703, filed on Jan. 30, 2019, now Pat. No. 10,759,851, which is a division of application No. 15/756,997, filed as application No. PCT/US2016/048508 on Aug. 25, 2016, now Pat. No. 10,294,294.

(60) Provisional application No. 62/216,400, filed on Jun. 10, 2015.

(51) Int. Cl.
| | | |
|---|---|---|
| C07K 16/18 | (2006.01) | |
| A61K 47/68 | (2017.01) | |
| C07K 16/00 | (2006.01) | |
| G01N 33/574 | (2006.01) | |
| A61K 9/127 | (2006.01) | |

(52) U.S. Cl.
CPC .............. *C07K 16/18* (2013.01); *A61K 9/127* (2013.01); *A61K 47/6843* (2017.08); *G01N 33/574* (2013.01); *C07K 16/005* (2013.01); *C07K 2317/10* (2013.01); *C07K 2317/24* (2013.01); *C07K 2317/55* (2013.01); *C07K 2317/565* (2013.01); *C07K 2317/622* (2013.01); *C07K 2317/76* (2013.01); *C07K 2317/92* (2013.01); *G01N 2500/04* (2013.01); *G01N 2510/00* (2013.01)

(58) Field of Classification Search
None
See application file for complete search history.

(56) References Cited

U.S. PATENT DOCUMENTS

| | | |
|---|---|---|
| 8,361,462 B2 | 1/2013 | Pandey et al. |
| 8,921,323 B2 | 12/2014 | Walensky et al. |
| 9,303,024 B2 | 4/2016 | Walensky et al. |
| 2015/0335671 A1 | 11/2015 | Gavathiotis et al. |
| 2016/0171150 A1 | 6/2016 | Walensky et al. |
| 2017/0114100 A1 | 4/2017 | Gavathiotis |
| 2019/0161537 A1 | 5/2019 | Gavathiotis et al. |

OTHER PUBLICATIONS

International Search Report for International Application No. PCT/US2016/48508 filed on Aug. 25, 2016; dated Nov. 15, 2016; 4 pages.
Written Opinion of the International Search Authority for International Application No. PCT/US2016/48508 filed on Aug. 25, 2016; dated Nov. 15, 2016; 4 pages.

*Primary Examiner* — Padmavathi Baskar
(74) *Attorney, Agent, or Firm* — Cantor Colburn LLP

(57) ABSTRACT

Synthetic fragment antigen-binding (Fab) antibodies are disclosed that bind to an N-terminal activation site of BCL-2-associated X-protein (BAX) and inhibit BAX activation. Also disclosed are methods of using the Fabs for measuring inactive monomeric BAX levels, screening for small molecules that bind to an N-terminal activation site of BAX, inhibiting apoptotic cell death, and predicting the ability of a cancer therapy to promote apoptotic cell death.

9 Claims, 11 Drawing Sheets

Specification includes a Sequence Listing.

| Clone | EC$_{50}$ (nM) | Sequences | | | |
|---|---|---|---|---|---|
| | | CDRL3 | CDRH1 | CDRH2 | CDRH3 |
| *Kabat numbering* | | 90.... | .30... | 50..a..55.. | 94 |
| 2B1 | 2.3 | QYSGSGHYLI | IYSSSM | SISSSSSYTS | RGYWYYWAWWASAMD |
| 3E8 | 2.6 | QSSYSLI | LSYYSM | SISPYYGYTY | RGGAYYFGYYGSGSYAMD |
| 3G11 | 5.5 | QWSFGPI | ISYYSM | SIYPYSSSTY | RSSAMD |
| 2D9 | 7.6 | QWSHYLI | LYYYSM | SISPSYGYTS | RSSFYYYALD |
| 3G9 | 9.5 | QHYYYSPWPI | LYSYYI | SISPYYSSTY | RSSYSYAGMD |
| 2C11 | 10 | QSYVSPI | ISSYYI | SISSYYSSTY | RVSYGHAYVGYSSGMD |
| 3H4 | 11 | QSWYYSYPI | LSYSSM | SISSYYSYTS | RYYGYGGGID |
| 2A6 | 13 | QSAGGYPLI | IYSSM | SISPYSSYTS | RSFGYGWAFD |
| 3H1 | 19 | QHSYPI | ISYSSI | SIYSYSGSTY | RYGAMD |
| 2A2 | 24 | QYYYPI | ISSSSI | SIYSYYGYTY | RYSAMD |
| 3G3 | 26 | QGAWSGGHLI | LSYSSM | YISPYYGYTY | RGWAYYYGYWGPSGLD |
| 2D5 | 46 | QWGYSHSHLI | ISYSSI | SISPYYGSTY | RSHFGALD |
| 2D2 | 66 | QSYYWVSPF | LYYSSI | SIYPYSGSTY | RSYGYAMD |
| 2A5 | 250 | QYHYWYYPI | ISYYSM | SISPYYGSTY | RAGAMD |

FIG. 1A

| | BLItz | | | ELISA |
|---|---|---|---|---|
| Fab | $k_a$ (M$^{-1}$s$^{-1}$) | $k_d$ (s$^{-1}$) | $K_D$ (nM) | EC$_{50}$ (nM) |
| 2B1 | 2.5 × 10$^5$ | 2.6 × 10$^{-3}$ | 10 | 2.3 |
| 3E8 | 2.9 × 10$^5$ | 7.5 × 10$^{-3}$ | 26 | 2.6 |
| 3G11 | 3.0 × 10$^5$ | 1.1 × 10$^{-2}$ | 38 | 5.5 |
| 2A5 | 5.4 × 10$^4$ | 9.1 × 10$^{-3}$ | 169 | 250 |

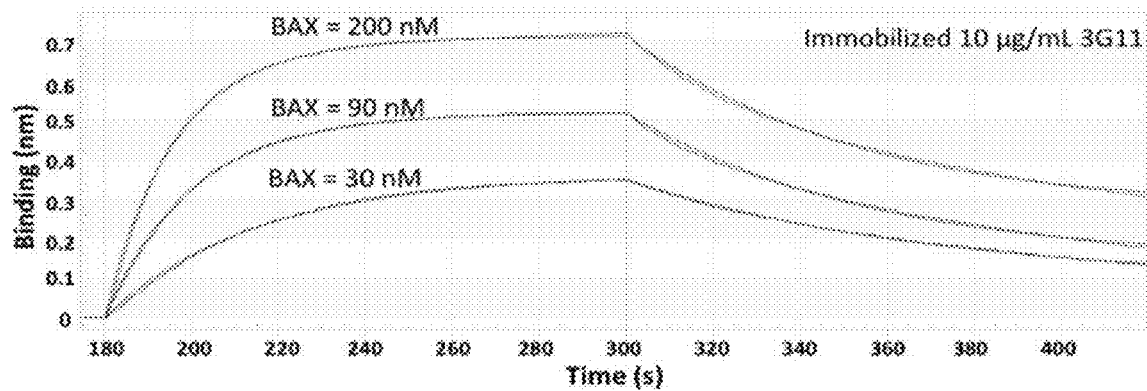

FIG. 1B

SYNTHETIC ANTIBODIES TO BAX AND USES THEREOF

CROSS-REFERENCE TO RELATED APPLICATIONS

This application is a divisional of U.S. patent application Ser. No. 16/261,703, filed on Jan. 30, 2019, which is a divisional of U.S. patent application Ser. No. 15/756,997, filed Mar. 2, 2018, which is a U.S. national stage entry under 35 U.S.C. § 371 of PCT International Patent Application No. PCT/US2016/048508, filed Aug. 25, 2016, which claims the benefit of U.S. Provisional Patent Application No. 62/216,400, filed Sep. 10, 2015, the contents of each of which are incorporated herein by reference into the subject application.

STATEMENT OF GOVERNMENT INTEREST

This invention was made with government support under grant numbers HL095929, CA178394 and CA155472 awarded by the National Institutes of Health. The government has certain rights in the invention.

BACKGROUND OF THE INVENTION

Throughout this application various publications are referred to by number in parentheses. Full citations for these references may be found at the end of the specification. The disclosures of these publications, and all patents, patent application publications and books referred to herein, are hereby incorporated by reference in their entirety into the subject application to more fully describe the art to which the subject invention pertains.

Apoptosis plays a critical role in maintaining normal tissue homoeostasis in multicellular organisms and its deregulation results in an imbalance of homeostasis contributing to several diseases (1, 2) The BCL-2 protein family plays a central role in regulating the mitochondrial pathway of apoptosis (3, 4) The mitochondrial outer membrane permeabilization (MOMP) is considered the key event that is regulated by the complex network of protein-protein interactions between pro-apoptotic and anti-apoptotic members of the BCL-2 family. Activation of pro-apoptotic members BAX and/or BAK is required for induction of MOMP, whereas the anti-apoptotic or survival proteins such as BCL-2, BCL-XL and MCL-1, inhibit the pro-apoptotic proteins and prevent MOMP. Activation of BAX and BAK or inhibition of anti-apoptotic BCL-2 proteins is regulated by direct interaction with the BH3-only proteins.

The activation pathway of BAX represents the gateway to apoptosis and understanding the function of BAX and its regulation mechanisms is an area of intensive investigation. BAX is predominantly found in the cytosolic compartment in an inactive conformation (5, 6). Upon cellular stress, BAX is triggered and undergoes a series of conformational changes that enable its translocation to the mitochondrial membrane and oligomerization leading to MOMP induction (7, 8). The structure of the BAX monomer in the inactive conformation was previously determined by nuclear magnetic resonance (NMR) spectroscopy (9). The inactive BAX structure adopts a typical BCL-2 fold, consisting of nine α-helices linked with variable loops. In contrast to BAK and anti-apoptotic BCL-2 proteins that reside at the mitochondrial outer membrane, the structure of BAX was determined with its hydrophobic C-terminal helix α9 bound to the canonical hydrophobic groove. When the C-terminal α9 helix dissociates from the canonical hydrophobic groove, it binds to the mitochondrial outer membrane facilitating the mitochondrial translocation of BAX (9). Structural analysis of a hydrocarbon stapled BIM BH3 helix bound to monomeric BAX uncovered an activation site at the N-terminal surface of BAX (10). This activation site regulates the trigger mechanism for conformational activation of cytosolic BAX leading to the release of the hydrophobic α9 helix and exposure of the hydrophobic α2 helix (BH3 domain) (10-12). Mitochondrial translocated BAX undergoes further conformational changes on the membrane that induce BAX oligomerization and MOMP (13-16), or is inhibited by anti-apoptotic Bcl-2 proteins (17-20).

A number of diseases and disorder are associated with premature or unwanted cell death and characterized by abnormal activation of BAX. The present invention addresses the need for inhibitors of BAX activation for therapeutic treatments.

SUMMARY OF THE INVENTION

The present invention discloses synthetic fragment antigen-binding (Fab) antibodies that bind to an N-terminal activation site of BCL-2-associated X-protein (BAX) and inhibit BAX activation. Also disclosed are methods of using the Fabs for measuring inactive monomeric BAX levels, screening for small molecules that bind to an N-terminal activation site of BAX, inhibiting apoptotic cell death, and predicting the ability of a cancer therapy to promote apoptotic cell death.

BRIEF DESCRIPTION OF THE DRAWINGS

FIG. 1A-1D. Discovery of synthetic antibody fragments that bind with high affinity to BAX at overlapping binding sites. (A) Synthetic antibody fragments (Fabs) that bind to BAX with the corresponding variable sequences of complementarity determining regions (CDRs) and half-maximal binding titers ($EC_{50}$) as determined by ELISA. (B) Top panel: Binding affinity ($K_D$), association rate constant ($k_a$) and dissociation rate constant ($k_d$) for select synthetic Fabs that bind to BAX as determined by biolayer interferometry. ELISA binding $EC_{50}$s are shown for comparison. Bottom panel: A representative biolayer interferometry experiment using immobilized 3G11 and three different BAX concentrations (C) Synthetic Fabs, except 2A5, compete biotinylated 3G11 (b3G11) from binding to BAX using a competitive ELISA. (D) Binding of selected phage-bound expressed Fabs (Φ) to BAX as competitively inhibited by the corresponding free synthetic Fab proteins (100 nM). All synthetic Fabs, except 2A5, show at least 40% competition efficacy to different phage-bound expressed Fabs. Data shown in (B-D) represent mean±SD from at least three independent experiments. In (A), SEQ ID NOs for CDRL3, CDRH1, CDRH2, and CDRH3 are respectively, SEQ ID NO:1-4 for Fab 2B1, SEQ ID NO:5-8 for 3E8, SEQ ID NO:9-12 for 3G11, SEQ ID NO:13-16 for 2D9, SEQ ID NO:17-20 for 3G9, SEQ ID NO:21-24 for 2C11, SEQ ID NO:25-28 for 3H4, SEQ ID NO:29-32 for 2A6, SEQ ID NO:33-36 for 3H1, SEQ ID NO:37-40 for 2A2, SEQ ID NO:41-44 for 3G3, SEQ ID NO:45-48 for 2D5, SEQ ID NO:49-52 for 2D2, and SEQ ID NO:53-56 for 2A5.

DETAILED DESCRIPTION OF THE INVENTION

Figure 1C:
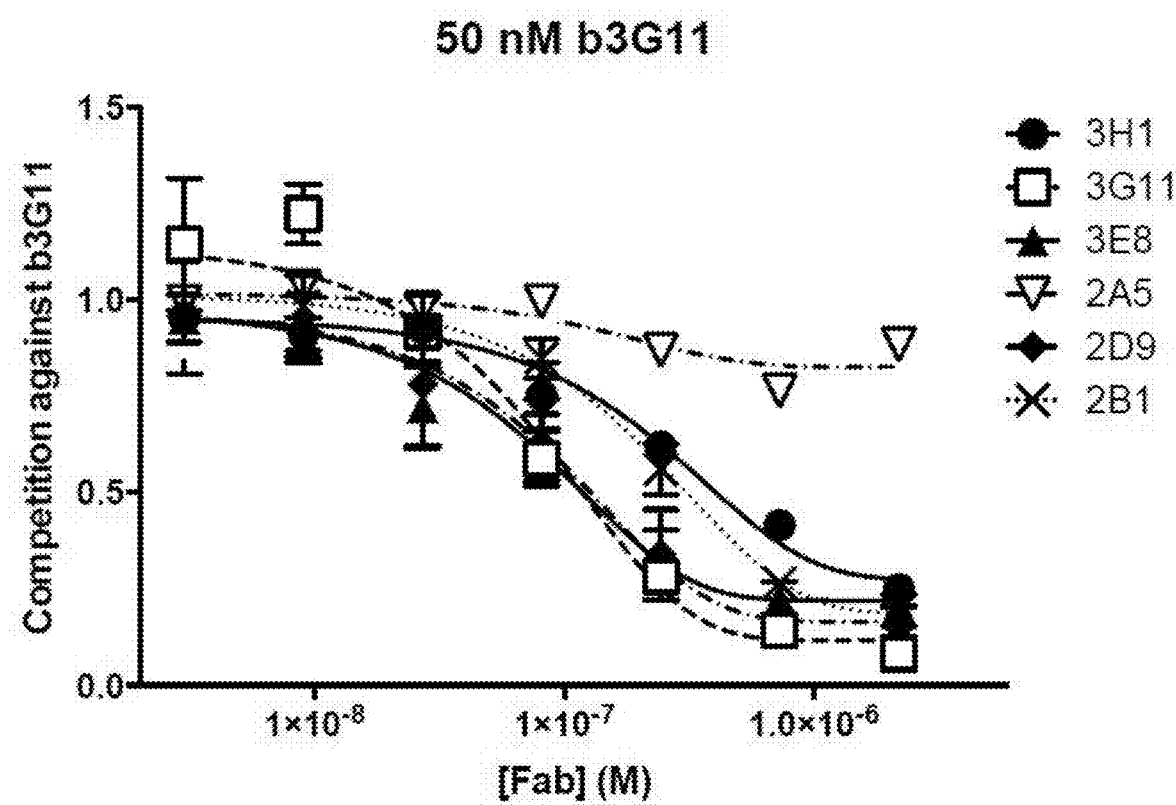

The invention provides a synthetic fragment antigen-binding (Fab) antibody that binds to an N-terminal activation site of BCL-2-associated X-protein (BAX) and inhibits BAX activation. Preferably, the antibody maintains BAX in its inactive, monomeric form. The antibody can bind to residues of helices α1 and α6, and to residues of α1-α2 loop of BAX. Preferably, the antibody binds to BAX with a half-maximal binding (EC$_{50}$) affinity of 2 nM-70 nM. Preferably, the antibody blocks the interaction of BAX with a BAX activating partner, such as, for example, tBID, PUMA, BIM and/or NOXA.

In different embodiments, the Fab is selected from the group consisting of

2B1 Fab, having a CDRL3 region comprising the amino acid sequence QYSGSGHYLI (SEQ ID NO:1), a CDRH1 region comprising the amino sequence IYSSSM (SEQ ID NO:2), a CDRH2 region comprising the amino acid sequence SISSSSSYTS (SEQ ID NO:3) and a CDRH3 region comprising the amino acid sequence RGYWYY-WAWWASAMD (SEQ ID NO:4);

3E8 Fab, having a CDRL3 region comprising the amino acid sequence QSSYSLI (SEQ ID NO:5), a CDRH1 region comprising the amino sequence LSYYSM (SEQ ID NO:6), a CDRH2 region comprising the amino acid sequence SISPYYGYTY (SEQ ID NO:7) and a CDRH3 region comprising the amino acid sequence RGGAYYFGYYGSGSYAMD (SEQ ID NO:8);

3G11 Fab, having a CDRL3 region comprising the amino acid sequence QWSFGPI (SEQ ID NO:9), a CDRH1 region comprising the amino sequence ISYYSM (SEQ ID NO:10), a CDRH2 region comprising the amino acid sequence SIYPYSSSTY (SEQ ID NO:11) and a CDRH3 region comprising the amino acid sequence RSSAMD (SEQ ID NO:12);

2D9 Fab, having a CDRL3 region comprising the amino acid sequence QWSHYLI (SEQ ID NO:13), a CDRH1 region comprising the amino sequence LYYYSM (SEQ ID NO:14), a CDRH2 region comprising the amino acid sequence SISPSYGYTS (SEQ ID NO:15) and a CDRH3 region comprising the amino acid sequence RSSFYYYALD (SEQ ID NO:16);

3G9 Fab, having a CDRL3 region comprising the amino acid sequence QHYYYSPWPI (SEQ ID NO:17), a CDRH1 region comprising the amino sequence LYSYYI (SEQ ID NO:18), a CDRH2 region comprising the amino acid sequence SISPYYSSTY (SEQ ID NO:19) and a CDRH3 region comprising the amino acid sequence RSSYSY-AGMD (SEQ ID NO:20);

2C11 Fab, having a CDRL3 region comprising the amino acid sequence QSYVSPI (SEQ ID NO:21), a CDRH1 region comprising the amino sequence ISSYYI (SEQ ID NO:22), a CDRH2 region comprising the amino acid sequence SISSYYSSTY (SEQ ID NO:23) and a CDRH3 region comprising the amino acid sequence RVSYGHAY-VGYSSGMD (SEQ ID NO:24);

3H4 Fab, having a CDRL3 region comprising the amino acid sequence QSWYYSYPI (SEQ ID NO:25), a CDRH1 region comprising the amino sequence LSYSSM (SEQ ID NO:26), a CDRH2 region comprising the amino acid sequence SISSYYSYTS (SEQ ID NO:27) and a CDRH3 region comprising the amino acid sequence RYYGYGG-GID (SEQ ID NO:28);

2A6 Fab, having a CDRL3 region comprising the amino acid sequence QSAGGYPLI (SEQ ID NO:29), a CDRH1 region comprising the amino sequence IYYSSM (SEQ ID NO:30), a CDRH2 region comprising the amino acid sequence SISPYSSYTS (SEQ ID NO:31) and a CDRH3 region comprising the amino acid sequence RSFGYG-WAFD (SEQ ID NO:32);

3H1 Fab, having a CDRL3 region comprising the amino acid sequence QHSYPI (SEQ ID NO:33), a CDRH1 region comprising the amino sequence ISYSSI (SEQ ID NO:34), a CDRH2 region comprising the amino acid sequence SIY- SYSGSTY (SEQ ID NO:35) and a CDRH3 region comprising the amino acid sequence RYGAMD (SEQ ID NO:36);

2A2 Fab, having a CDRL3 region comprising the amino acid sequence QYYYPI (SEQ ID NO:37), a CDRH1 region comprising the amino sequence ISSSSI (SEQ ID NO:38), a CDRH2 region comprising the amino acid sequence SIYSYYGYTY (SEQ ID NO:39) and a CDRH3 region comprising the amino acid sequence RYSAMD (SEQ ID NO:40);

3G3 Fab, having a CDRL3 region comprising the amino acid sequence QGAWSGGHLI (SEQ ID NO:41), a CDRH1 region comprising the amino sequence LSYSSM (SEQ ID NO:42), a CDRH2 region comprising the amino acid sequence YISPYYGYTY (SEQ ID NO:43) and a CDRH3 region comprising the amino acid sequence RGWAYYYGYWGPSGLD (SEQ ID NO:44);

2D5 Fab, having a CDRL3 region comprising the amino acid sequence QWGYSHSHLI (SEQ ID NO:45), a CDRH1 region comprising the amino sequence ISYSS (SEQ ID NO:46), a CDRH2 region comprising the amino acid sequence SISPYYGSTY (SEQ ID NO:47) and a CDRH3 region comprising the amino acid sequence RSHFGALD (SEQ ID NO:48);

2D2 Fab, having a CDRL3 region comprising the amino acid sequence QSYYWVSPF (SEQ ID NO:49), a CDRH1 region comprising the amino sequence LYYSSI (SEQ ID NO:50), a CDRH2 region comprising the amino acid sequence SIYPYSGSTY (SEQ ID NO:51) and a CDRH3 region comprising the amino acid sequence RSYGYAMD (SEQ ID NO:52); and 2A5 Fab, having a CDRL3 region comprising the amino acid sequence QYHYWYYPI (SEQ ID NO:53), a CDRH1 region comprising the amino sequence ISYYSM (SEQ ID NO:54), a CDRH2 region comprising the amino acid sequence SISPYYGSTY (SEQ ID NO:55) and a CDRH3 region comprising the amino acid sequence RAGAMD (SEQ ID NO:56).

The complete heavy and light chain variable domain amino acid sequences for the 14 Fabs are shown below.

1) 3E8
heavy chain, 242 residues
(SEQ ID NO: 58)
EVQLVESGGGLVQPGGSLRLSCAASGFNLSYYSMHWVRQAPGKGLEWVAS

ISPYYGYTYYADSVKGRFTISADTSKNTAYLQMNSLRAEDTAVYYCARGG

AYYFGYYGSGSYAMDYWGQGTLVTVSSASTKGPSVFPLAPSSKSTSGGTA

ALGCLVKDYFPEPVTVSWNSGALTSGVHTFPAVLQSSGLYSLSSVVTVPS

SSLGTQTYICNVNHKPSNTKVDKKVEPKSCDKTHTCHHHHHH light chain, 225 residues
(SEQ ID NO: 59)
DIQMTQSPSSLSASVGDRVTITCRASQSVSSAVAWYQQKPGKAPKLLIYS

ASSLYSGVPSRFSGSRSGTDFTLTISSLQPEDFATYYCQQSSYS~~~LIT

FGQGTKVEIKRTVAAPSVFIFPPSDSQLKSGTASVVCLLNNFYPREAKVQ

WKVDNALQSGNSQESVTEQDSKDSTYSLSSTLTLSKADYEKHKVYACEVT

HQGLSSPVTKSFNRGECGGSDYKDDDDK 2) 3G3
heavy chain, 240 residues
(SEQ ID NO: 60)
EVQLVESGGGLVQPGGSLRLSCAASGFNLSYSSMHWVRQAPGKGLEWVAY

ISPYYGYTYYADSVKGRFTISADTSKNTAYLQMNSLRAEDTAVYYCARGW

AYYYGYWGPS~~GLDYWGQGTLVTVSSASTKGPSVFPLAPSSKSTSGGTA

ALGCLVKDYFPEPVTVSWNSGALTSGVHTFPAVLQSSGLYSLSSVVTVPS

SSLGTQTYICNVNHKPSNTKVDKKVEPKSCDKTHTC HHHHHH light chain, 228 residues
(SEQ ID NO: 61)
DIQMTQSPSSLSASVGDRVTITCRASQSVSSAVAWYQQKPGKAPKLLIYS

ASSLYSGVPSRFSGSRSGTDFTLTISSLQPEDFATYYCQQGAWSGGHLIT

FGQGTKVEIKRTVAAPSVFIFPPSDSQLKSGTASVVCLLNNFYPREAKVQ

WKVDNALQSGNSQESVTEQDSKDSTYSLSSTLTLSKADYEKHKVYACEVT

HXGLSSPVTKSFNRGECGGSDYKDDDDK 3) 3G9
heavy chain, 234 residues
(SEQ ID NO: 62)
EVQLVESGGGLVQPGGSLRLSCAASGFNLYSYYIHWVRQAPGKGLEWVAS

ISPYYSSTYYADSVKGRFTISADTSKNTAYLQMNSLRAEDTAVYYCARSS

YSYA~~~~~~~~GMDYWGQGTLVTVSSASTKGPSVFPLAPSSKSTSGGTA

ALGCLVKDYFPEPVTVSWNSGALTSGVHTFPAVLQSSGLYSLSSVVTVPS

SSLGTQTYICNVNHKPSNTKVDKKVEPKSCDKTHTC HHHHHH light chain, 228 residues
(SEQ ID NO: 63)
DIQMTQSPSSLSASVGDRVTITCRASQSVSSAVAWYQQKPGKAPKLLIYS

ASSLYSGVPSRFSGSRSGTDFTLTISSLQPEDFATYYCQQHYYYSPWIT

FGQGTKVEIKRTVAAPSVFIFPPSDSQLKSGTASVVCLLNNFYPREAKVQ

WKVDNALQSGNSQESVTEQDSKDSTYSLSSTLTLSKADYEKHKVYACEVT

HQGLSSPVTKSFNRGECGGSDYKDDDDK 4) 3G11
heavy chain, 230 residues
(SEQ ID NO: 64)
EVQLVESGGGLVQPGGSLRLSCAASGFNISYYSMHWVRQAPGKGLEWVAS

IYPYSSSTYYADSVKGRFTISADTSKNTAYLQMNSLRAEDTAVYYCARSS

~~~~~~~~~~~AMDYWGQGTLVTVSSASTKGPSVFPLAPSSKSTSGGTA

ALGCLVKDYFPEPVTVSWNSGALTSGVHTFPAVLQSSGLYSLSSVVTVPS

SSLGTQTYICNVNHKPSNTKVDKKVEPKSCDKTHTCHHHHHH light chain, 225 residues
(SEQ ID NO: 65)
DIQMTQSPSSLSASVGDRVTITCRASQSVSSAVAWYQQKPGKAPKLLIYS

ASSLYSGVPSRFSGSRSGTDFTLTISSLQPEDFATYYCQQWSFG~~~PIT

FGQGTKVEIKRTVAAPSVFIFPPSDSQLKSGTASVVCLLNNFYPREAKVQ

WKVDNALQSGNSQESVTEQDSKDSTYSLSSTLTLSKADYEKHKVYACEVT

HQGLSSPVTKSFNRGECGGSDYKDDDDK 5) 3H1
heavy chain, 230 residues
(SEQ ID NO: 66)
EVQLVESGGGLVQPGGSLRLSCAASGFNISYSSIHWVRQAPGKGLEWVAS

IYSYSGSTYYADSVKGRFTISADTSKNTAYLQMNSLRAEDTAVYYCARYG

~~~~~~~~~~~AMDYWGQGTLVTVSSASTKGPSVFPLAPSSKSTSGGTA

ALGCLVKDYFPEPVTVSWNSGALTSGVHTFPAVLQSSGLYSLSSVVTVPS

SSLGTQTYICNVNHKPSNTKVDKKVEPKSCDKTHTCHHHHHH light chain, 224 residues
(SEQ ID NO: 67)
DIQMTQSPSSLSASVGDRVTITCRASQSVSSAVAWYQQKPGKAPKLLIYS
ASSLYSGVPSRFSGSRSGTDFTLTISSLQPEDFATYYCQQHSY~~~~PIT
FGQGTKVEIKRTVAAPSVFIFPPSDSQLKSGTASVVCLLNNFYPREAKVQ
WKVDNALQSGNSQESVTEQDSKDSTYSLSSTLTLSKADYEKHKVYACEVT
HQGLSSPVTKSFNRGECGGSDYKDDDDK 6) 3H4
heavy chain, 234 residues
(SEQ ID NO: 68)
EVQLVESGGGLVQPGGSLRLSCAASGFNLSYSSMHWVRQAPGKGLEWVAS
ISSYYSYTSYADSVKGRFTISADTSKNTAYLQMNSLRAEDTAVYYCARYY
GYGG~~~~~~~~GIDYWGQGTLVTVSSASTKGPSVFPLAPSSKSTSGGTA
ALGCLVKDYFPEPVTVSWNSGALTSGVHTFPAVLQSSGLYSLSSVVTVPS
SSLGTQTYICNVNHKPSNTKVDKKVEPKSCDKTHTC HHHHHH light chain, 227 residues
(SEQ ID NO: 69)
DIQMTQSPSSLSASVGDRVTITCRASQSVSSAVAWYQQKPGKAPKLLIYS
ASSLYSGVPSRFSGSRSGTDFTLTISSLQPEDFATYYCQQSWYYSY~PIT
FGQGTKVEIKRTVAAPSVFIFPPSDSQLKSGTASVVCLLNNFYPREAKVQ
WKVDNALQSGNSQESVTEQDSKDSTYSLSSTLTLSKADYEKHKVYACEVT
HQGLSSPVTKSFNRGECGGSDYKDDDDK 7) 2A2
heavy chain, 230 residues
(SEQ ID NO: 70)
EVQLVESGGGLVQPGGSLRLSCAASGFNISSSSIHWVRQAPGKGLEWVAS
IYSYYGYTYYADSVKGRFTISADTSKNTAYLQMNSLRAEDTAVYYCARYS
~~~~~~~~~~~AMDYWGQGTLVTVSSASTKGPSVFPLAPSSKSTSGGTA
ALGCLVKDYFPEPVTVSWNSGALTSGVHTFPAVLQSSGLYSLSSVVTVPS
SSLGTQTYICNVNHKPSNTKVDKKVEPKSCDKTHTC HHHHHH light chain, 224 residues
(SEQ ID NO: 71)
DIQMTQSPSSLSASVGDRVTITCRASQSVSSAVAWYQQKPGKAPKLLIYS
ASSLYSGVPSRFSGSRSGTDFTLTISSLQPEDFATYYCQQYYY~~~~PIT
FGQGTKVEIKRTVAAPSVFIFPPSDSQLKSGTASVVCLLNNFYPREAKVQ
WKVDNALQSGNSQESVTEQDSKDSTYSLSSTLTLSKADYEKHKVYACEVT
HQGLSSPVTKSFNRGECGGSDYKDDDDK 8) 2A5
heavy chain, 230 residues
(SEQ ID NO: 72)
EVQLVESGGGLVQPGGSLRLSCAASGFNIYSSSMHWVRQAPGKGLEWVAS
ISSSSSYTSYADSVKGRFTISADTSKNTAYLQMNSLRAEDTAVYYCAR~A
G~~~AMDYWGQGTLVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTC HHHHHH light chain, 227 residues
(SEQ ID NO: 73)
DIQMTQSPSSLSASVGDRVTITCRASQSVSSAVAWYQQKPGKAPKLLIYS
ASSLYSGVPSRFSGSRSGTDFTLTISSLQPEDFATYYCQQYHYWYY~PIT
FGQGTKVEIKRTVAAPSVFIFPPSDSQLKSGTASVVCLLNNFYPREAKVQ
WKVDNALQSGNSQESVTEQDSKDSTYSLSSTLTLSKADYEKHKVYACEVT
HXGLSSPVTKSFNRGECGGSDYKDDDDK 9) 2A6
heavy chain, 234 residues
(SEQ ID NO: 74)
EVQLVESGGGLVQPGGSLRLSCAASGFNIYYSSMHWVRQAPGKGLEWVAS
ISPYSSYTSYADSVKGRFTISADTSKNTAYLQMNSLRAEDTAVYYCARSF
GYGW~~~~~~~~AFDYWGQGTLVTVSSASTKGPSVFPLAPSSKSTSGGTA
ALGCLVKDYFPEPVTVSWNSGALTSGVHTFPAVLQSSGLYSLSSVVTVPS
SSLGTQTYICNVNHKPSNTKVDKKVEPKSCDKTHTC HHHHHH light chain, 227 residues
(SEQ ID NO: 75)
DIQMTQSPSSLSASVGDRVTITCRASQSVSSAVAWYQQKPGKAPKLLIYS
ASSLYSGVPSRFSGSRSGTDFTLTISSLQPEDFATYYCQQSAGGYP~LIT
FGQGTKVEIKRTVAAPSVFIFPPSDSQLKSGTASVVCLLNNFYPREAKVQ
WKVDNALQSGNSQESVTEQDSKDSTYSLSSTLTLSKADYEKHKVYACEVT
HXGLSSPVTKSFNRGECGGSDYKDDDDK 10) 2B1
heavy chain, 239 residues
(SEQ ID NO: 76)
EVQLVESGGGLVQPGGSLRLSCAASGFNIYSSSMHWVRQAPGKGLEWVAS
ISSSSSYTSYADSVKGRFTISADTSKNTAYLQMNSLRAEDTAVYYCARGY
WYYWAWWAS~~~AMDYWGQGTLVTVSSASTKGPSVFPLAPSSKSTSGGTA
ALGCLVKDYFPEPVTVSWNSGALTSGVHTFPAVLQSSGLYSLSSVVTVPS
SSLGTQTYICNVNHKPSNTKVDKKVEPKSCDKTHTC HHHHHH light chain, 228 residues
(SEQ ID NO: 77)
DIQMTQSPSSLSASVGDRVTITCRASQSVSSAVAWYQQKPGKAPKLLIYS
ASSLYSGVPSRFSGSRSGTDFTLTISSLQPEDFATYYCQQYSGSGHYLIT
FGQGTKVEIKRTVAAPSVFIFPPSDSQLKSGTASVVCLLNNFYPREAKVQ
WKVDNALQSGNSQESVTEQDSKDSTYSLSSTLTLSKADYEKHKVYACEVT
HQGLSSPVTKSFNRGECGGSDYKDDDDK 11) 2C11
heavy chain, 240 residues
(SEQ ID NO: 78)
EVQLVESGGGLVQPGGSLRLSCAASGFNISSYYIHWVRQAPGKGLEWVAS
ISSYYSSTYYADSVKGRFTISADTSKNTAYLQMNSLRAEDTAVYYCARVS
YGHAYVGYSS~~GMDYWGQGTLVTVSSASTKGPSVFPLAPSSKSTSGGTA
ALGCLVKDYFPEPVTVSWNSGALTSGVHTFPAVLQSSGLYSLSSVVTVPS
SSLGTQTYICNVNHKPSNTKVDKKVEPKSCDKTHTC HHHHHH light chain, 225 residues
(SEQ ID NO: 79)
DIQMTQSPSSLSASVGDRVTITCRASQSVSSAVAWYQQKPGKAPKLLIYS
ASSLYSGVPSRFSGSRSGTDFTLTISSLQPEDFATYYCQQSYVS~~~PIT
FGQGTKVEIKRTVAAPSVFIFPPSDSQLKSGTASVVCLLNNFYPREAKVQ
WKVDNALQSGNSQESVTEXDSKDSTYSLSSTLTLSKADYEKHKVYACEVT
HXGLSSPVTKSFNRGECGGSDYKDDDDK -continued 12) 2D2
heavy chain, 232 residues
(SEQ ID NO: 80)
EVQLVESGGGLVQPGGSLRLSCAASGFNLYYSSIHWVRQAPGKGLEWVAS

IYPYSGSTYYADSVKGRFTISADTSKNTAYLQMNSLRAEDTAVYYCARSY

GY~~~~~~~~~~AMDYWGQGTLVTVSSASTKGPSVFPLAPSSKSTSGGTA

ALGCLVKDYFPEPVTVSWNSGALTSGVHTFPAVLQSSGLYSLSSVVTVPS

SSLGTQTYICNVNHKPSNTKVDKKVEPKSCDKTHTC HHHHHH light chain, 227 residues
(SEQ ID NO: 81)

DIQMTQSPSSLSASVGDRVTITCRASQSVSSAVAWYQQKPGKAPKLLIYS

ASSLYSGVPSRFSGSRSGTDFTLTISSLQPEDFATYYCQQSYYWVS~PFT

FGQGTKVEIKRTVAAPSVFIFPPSDSQLKSGTASVVCLLNNFYPREAKVQ

WKVDNALQSGNSQESVTEQDSKDSTYSLSSTLTLSKADYEKHKVYACEVT

HQGLSSPVTKSFNRGECGGSDYKDDDDK 13) 2D5
heavy chain, 232 residues
(SEQ ID NO: 82)

EVQLVESGGGLVQPGGSLRLSCAASGFNISYSSIHWVRQAPGKGLEWVAS

ISPYYGSTYYADSVKGRFTISADTSKNTAYLQMNSLRAEDTAVYYCARSH

FG~~~~~~~~~~ALDYWGQGTLVTVSSASTKGPSVFPLAPSSKSTSGGTA

ALGCLVKDYFPEPVTVSWNSGALTSGVHTFPAVLQSSGLYSLSSVVTVPS

SSLGTQTYICNVNHKPSNTKVDKKVEPKSCDKTHTC HHHHHH light chain, 228 residues
(SEQ ID NO: 83)

DIQMTQSPSSLSASVGDRVTITCRASQSVSSAVAWYQQKPGKAPKLLIYS

ASSLYSGVPSRFSGSRSGTDFTLTISSLQPEDFATYYCQQWGYSHSHLIT

FGQGTKVEIKRTVAAPSVFIFPPSDSQLKSGTASVVCLLNNFYPREAKVQ

WKVDNALQSGNSQESVTEQDSKDSTYSLSSTLTLSKADYEKHKVYACEVT

HXGLSSPVTKSFNRGECGGSDYKDDDDK 14) 2D9
heavy chain, 234 residues
(SEQ ID NO: 84)

EVQLVESGGGLVQPGGSLRLSCAASGFNLYYYSMHWVRQAPGKGLEWVAS

ISPSYGYTSYADSVKGRFTISADTSKNTAYLQMNSLRAEDTAVYYCARSS

FYYY~~~~~~~~ALDYWGQGTLVTVSSASTKGPSVFPLAPSSKSTSGGTA

ALGCLVKDYFPEPVTVSWNSGALTSGVHTFPAVLQSSGLYSLSSVVTVPS

SSLGTQTYICNVNHKPSNTKVDKKVEPKSCDKTHTC HHHHHH light chain, 225 residues
(SEQ ID NO: 85)

DIQMTQSPSSLSASVGDRVTITCRASQSVSSAVAWYQQKPGKAPKLLIYS

ASSLYSGVPSRFSGSRSGTDFTLTISSLQPEDFATYYCQQWSHY~~~LIT

FGQGTKVEIKRTVAAPSVFIFPPSDSQLKSGTASVVCLLNNFYPREAKVQ

WKVDNALQSGNSQESVTEQDSKDSTYSLSSTLTLSKADYEKHKVYACEVT

HQGLSSPVTKSFNRGECGGSDYKDDDDK.

The Fabs bind to and inhibit BAX.

The Fabs can be produced reproducibly in large amounts using bacterial expression or mammalian expression systems.

The invention further provides a method of inhibiting apoptotic cell death by contacting BCL-2-associated X-protein (BAX) with any of the synthetic Fab antibodies disclosed herein in an amount effective to inhibit activation of BAX and apoptotic cell death. The synthetic Fab antibody can be conjugated to a therapeutic agent and/or to an agent that facilitates transport across a cell membrane. The synthetic Fab antibody can administered to a subject using any known method effective to administer an amount of the antibody that inhibits activation of BAX, including, for example, lentiviral or adenoviral expression, a plasmid, nanoparticles or liposomes.

The synthetic Fab antibody can be administered to a subject having, for example, a disease or disorder selected from the group consisting of a cardiovascular disease or disorder (e.g., arteriosclerosis, heart failure, heart transplantation, aneurism, chronic pulmonary disease, ischemic heart disease, hypertension, thrombosis, and/or cardiomyopathies), a neurodegenerative or neurological disease or disorder (e.g., Alzheimer's disease, Parkinson's disease, Huntington's disease, retinitis pigmentosa, spinal muscular atrophy, various forms of cerebellar degeneration, and/or amyotrophic lateral sclerosis), a liver disease or disorder, a kidney disease or disorder, a metabolic disease or disorder, an immunological disorder (e.g., organ transplant rejection, arthritis, lupus, IBD, Crohn's disease, asthma, multiple sclerosis, and/or diabetes), ischemia (e.g., stroke, myocardial infarction and/or reperfusion injury), infertility, a blood disorder (e.g., fanconi anemia, aplastic anemia, thalassemia, congenital neutropenia, and/or myelodysplasia), renal hypoxia, diabetes, hepatitis, asthma and AIDS.

Also provided is a method for measuring inactive monomeric BAX levels in a tissue sample from a subject comprising contacting the sample with any of the synthetic Fab antibodies disclosed herein and measuring the amount of antibody bound to the sample, wherein the amount of bound antibody is indicative of the level of inactive monomeric BAX in the tissue sample.

Further provided is a method for screening for small molecules that bind to an N-terminal activation site of BAX comprising contacting BAX with any of the synthetic Fab antibodies disclosed herein in the presence and in the absence of a small molecule and measuring the amount of antibody that binds to BAX, wherein a decrease in the amount of antibody binding to BAX in the presence of the small molecule indicates that the small molecule is a candidate for binding to the N-terminal activation site of BAX. It is also possible that the small molecule binds to a site on BAX that causes allosteric conformational changes that cause a decrease in the amount of antibody binding to BAX.

The method can comprise a competitive ELISA screening assay. In an embodiment of the methods described herein, the methods are useful for identifying therapeutic cell death inhibitors. In an embodiment of the methods described herein, the methods are useful for identifying therapeutic cell death activators.

In an embodiment of the methods described herein, the small molecule has a molecular weight of 2000 daltons or less. In an embodiment of the methods described herein, the small molecule has a molecular weight of 1500 daltons or less. In an embodiment of the methods described herein, the small molecule has a molecular weight of 1000 daltons or less. In an embodiment of the methods described herein, the small molecule has a molecular weight of 800 daltons or less. In an embodiment of the methods described herein, the small molecule has a molecular weight of either 2000, 1500, 1000, 800, 700, 600, 500 or 400 daltons or less. In an embodiment of the methods described herein, the small molecule is a small organic molecule.

Still further provided is a method of predicting the ability of a cancer therapy to promote apoptotic cell death comprising contacting a cancerous tissue sample with any of the synthetic Fab antibodies disclosed herein, with and without the cancer therapy, and measuring the amount of antibody that binds to the tissue sample, wherein a decrease in the amount of bound antibody with the cancer therapy indicates that the cancer therapy promotes activation of BAX and apoptotic cell death, and the amount of bound antibody without the cancer therapy can predict the capacity of the cancer therapy to promote activation of BAX and apoptotic cell death in the cancerous tissue.

In the methods disclosed herein, the synthetic Fab antibody can be labeled with a detectable label, such as a fluorescent label or a radioactive label. The antibody can be biotinylated.

As used herein, "BAX" is BCL-2-associated X-protein. In an embodiment, the BAX is mammalian. In a preferred embodiment, the BAX is a human BAX. In an embodiment, the BAX comprises consecutive amino acid residues having the following sequence:

```
                                        (SEQ ID NO: 57, human)
MDGSGEQPRGGGPTSSEQIMKTGALLLQGFIQDRAGRMGGEAPELALDPV

PQDASTKKLSECLKRIGDELDSNMELQRMIAAVDTDSPREVFFRVAADMF

SDGNFNWGRVVALFYASKLVLKALCTKVPELIRTIMGWTLDFLRERLLG

WIQDQGGWDGLLSYFGTPTWQTVTIFVAGVLTASLTIWKKMG.
```

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

Synthetic antibody technology was applied to BCL-2 family proteins to probe novel conformations and functional regions on the surface of BAX. Synthetic antibody discovery utilizes diversity targeted to the antibody complementarity determining regions (CDRs) that is encoded by designed, synthetic oligonucleotides and screened by phage or yeast display (22, 23). Since library construction and selection is performed entirely in vitro, the state of the target can be controlled through the antibody discovery process. Therefore, the specificity of the output antibodies can be tuned to user-specified stringency (24, 25). Using a phage display screen, synthetic antibodies were identified that bind with high affinity and specificity to BAX. Although BAX can be expressed and purified readily, and studied by NMR and other biophysical techniques, it is prone to aggregation under some conditions (such as detergents). This aggregation phenomenon is presumably linked to its function of forming oligomeric pores in the mitochondrial membrane, but presents a formidable challenge in raising conformation-specific antibodies using techniques requiring immunization. Thus, there was a strong rationale for utilizing in vitro selection.

Antibodies were identified that can be used as structural and biochemical probes to dissect key regulatory mechanisms and conformations of BAX (26, 27). Fourteen novel synthetic antibody fragments (Fabs) were identified that specifically target BAX. These synthetic Fabs have no significant homology in the CDR sequences suggesting a diversity of molecular interactions with BAX. They bind to BAX with nanomolar affinities and occupy overlapping binding sites on BAX. Additionally, the synthetic Fabs inhibit BAX in assays using liposomal membranes or isolated mitochondria. Further analysis using isolated mitochondria suggest that the Fabs bind to cytosolic BAX and inhibit its ability to translocate and insert onto the mitochondria outer membrane. Structural studies using NMR and hydrogen/deuterium exchange mass spectrometry showed that a representative synthetic Fab (3G11) forms a stoichiometric and stable complex with monomeric and inactive BAX, with a binding site that involves residues of helices $\alpha 1/\alpha 6$ and of the $\alpha 1$-$\alpha 2$ loop. Therefore, binding of the synthetic Fabs overlaps with the N-terminal activation site of BAX suggesting a novel mechanism of BAX inhibition through direct competition with the BAX activation process. These Fabs provide new tools for probing BAX activity in an unparalleled manner and provide a strategy for therapeutic inhibition of BAX in disease.

Materials and Methods

Production of Recombinant BAX—

Human full-length wild type BAX, truncated $\alpha 9$ BAX (BAX $\Delta$C) and BAX mutants in pTYB1 vector (New England Biolabs) were expressed in BL21 CodonPlus (DE3)-RIPL+$E.$ $coli$ strain and purified as previously described (9, 10).

Fab Protein Expression—

The phage display vectors for the 14 identified clones were converted to Fab protein expression vectors by insertion of a stop codon and a 6-Histidine tag upstream of the P3 gene fusion. Fab proteins were expressed periplasmically in $E.$ $coli$ BL21(DE3) (New England Biolabs, Ipswich, Mass.) by growth in low-phosphate media at 30° C. for 18-22 h. The cells were harvested by centrifugation and lysed by using the BugBuster lysis reagent according to the manufacturer's instructions (Novagen, Madison, Wis.). The lysate was subjected to centrifugation, and the supernatant was applied to a nickel column (Ni-NTA resin, Qiagen, Valencia, Calif.) pre-equilibrated with Tris-buffered saline (TBS), pH 7. The Fab-bound Ni-NTA column was then washed with 20-column volume TBS buffer with 20 mM imidazole. Next, the protein was eluted with TBS buffer with 250 mM imidazole. The eluent was dialyzed into PBS at pH 8.0, and applied to a Protein A affinity column (beads from Pierce Thermo Scientific, Rockford, Ill.) for further purification. The Fab-bound beads were washed with PBS, pH 8.0 (15 column volumes), and the Fab proteins were eluted with 100 mM glycine, pH 2.0. The eluted Fab proteins were immediately neutralized to ~pH 7 using 1 M Tris buffer, pH 8.0. Fractions containing the Fab proteins were buffer-exchanged into PBS, pH 7.0 and were used directly in following binding and activity assays, or flash-frozen and stored at 80° C. for future use. The Fab protein concentrations were determined by measuring the absorbance at 280 nm. The extinction coefficients at 280 nm were calculated from the Fab protein sequences using ExPASy.

Origin of Sequence of the CDR Regions—

The antibody framework of all the BAX antibodies is a common scaffold based on Herceptin (mAb 4D5), which is a humanized variant of a mouse anti-Her2 monoclonal antibody developed by Genentech (South San Francisco, Calif.). The complementarity determining regions (CDRs), which bind the antigen and provide the mAb specificity, contain wholely "synthetic" (artificial) sequences. The nature of these synthetic CDR sequences reflects the engineered nature of the phage antibody library from which the antibodies were obtained: Koellhoffer et al., Chembiochem, 2012, 13, 2549.

Sequences of Antibodies Expressed in Cells—

The BAX antibodies were converted to single chain variable fragments (scFvs) and cloned into cell expression plasmids (discussed below). DNA sequences for the scFv open reading frames are indicated below for different Fabs:

3E8,
SEQ ID NO: 86
GGATCCGACATCCAGATGACCCAGTCCCCAAGCTCCCTGAGCGCATCCGT
GGGCGATAGGGTGACCATCACATGCAGGGCATCTCAGAGCGTGTCTAGCG
CAGTGGCATGGTACCAGCAGAAGCCAGGCAAGGCCCCTAAGCTGCTGATC
TACAGCGCCTCCTCTCTGTATTCCGGAGTGCCTTCTCGGTTCTCCGGCAG
CCGGAGCGGAACCGACTTTACCCTGACAATCAGCTCCCTGCAGCCAGAGG
ATTTCGCCACATACTATTGCCAGCAGTCTAGCTACTCCCTGATCACCTTT
GGCCAGGGCACAAAGGTGGAGATCAAGGGAGGAGGCAGCGGAGGAGGCTC
CGGAGGCGGCTCTGAGGTGCAGCTGGTGGAGAGCGGAGGAGGACTGGTGC
AGCCTGGAGGCAGCCTGAGGCTGTCCTGTGCAGCATCTGGCTTCAACCTG
TCTTACTATAGCATGCACTGGGTGCGCCAGGCACCAGGCAAGGGCCTGGA
GTGGGTGGCCTCCATCTCTCCCTACTATGGCTACACCTACTATGCCGACT
CTGTGAAGGGCCGGTTCACAATCAGCGCCGATACCTCCAAGAACACAGCC
TATCTGCAGATGAATAGCCTGAGGGCAGAGGACACCGCAGTGTACTATTG
TGCCAGAGGCGGCGCCTACTATTTTGGCTACTATGGCAGCGGCTCCTACG
CCATGGATTATTGGGGCCAGGGCACCCTGGTGACAGTGTCCTCTTAATCT
AGA

3G11,
SEQ ID NO: 87
GGATCCGACATCCAGATGACCCAGAGCCCAAGCTCCCTGAGCGCATCCGT
GGGCGATAGGGTGACCATCACATGCAGGGCATCTCAGAGCGTGTCTAGCG
CAGTGGCATGGTACCAGCAGAAGCCAGGCAAGGCCCCTAAGCTGCTGATC
TACTCCGCCTCCTCTCTGTATAGCGGCGTGCCTTCCCGGTTCTCCGGCAG
CCGGAGCGGAACCGACTTTACCCTGACAATCAGCTCCCTGCAGCCTGAGG
ATTTCGCCACATACTATTGCCAGCAGTGGAGCTTCGGCCCAATCACCTTT
GGCCAGGGCACAAAGGTGGAGATCAAGGGAGGAGGCTCTGGAGGAGGCAG
CGGAGGCGGCTCCGAGGTGCAGCTGGTGGAGTCCGGCGGCGGCCTGGTGC
AGCCAGGAGGCTCTCTGAGGCTGAGCTGTGCCGCCTCCGGCTTCAACATC
TCCTACTATTCTATGCACTGGGTGCGCCAGGCACCAGGCAAGGGCCTGGA
GTGGGTGGCCTCCATCTACCCCTATTCTAGCTCCACCTACTATGCCGACT
CTGTGAAGGGCCGGTTTACAATCTCTGCCGATACCAGCAAGAACACAGCC
TACCTGCAGATGAATAGCCTGAGGGCAGAGGACACCGCAGTGTACTATTG
TGCCAGATCTAGCGCCATGGATTATTGGGGCCAGGGCACCCTGGTGACAG
TGTCCTCTTAATCTAGA

3H1,
SEQ ID NO: 88
GGATCCGACATCCAGATGACCCAGAGCCCAAGCTCCCTGAGCGCATCCGT
GGGCGATAGGGTGACCATCACATGCAGGGCATCTCAGAGCGTGTCTAGCG
CAGTGGCATGGTACCAGCAGAAGCCAGGCAAGGCCCCTAAGCTGCTGATC
TACAGCGCCTCCTCTCTGTATTCCGGAGTGCCTTCTCGGTTCTCCGGCAG
CCGGAGCGGAACCGACTTTACCCTGACAATCAGCTCCCTGCAGCCAGAGG
ATTTCGCCACATACTATTGCCAGCAGCACTCCTACCCCATCACCTTTGGC
CAGGGCACAAAGGTGGAGATCAAGGGAGGAGGCAGCGGAGGAGGCTCCGG
AGGCGGCTCTGAGGTGCAGCTGGTGGAGTCCGGAGGAGGACTGGTGCAGC
CTGGAGGCAGCCTGAGGCTGTCCTGTGCAGCATCTGGCTTCAACATCTCT
TACTCTAGCATCCACTGGGTGCGCCAGGCACCAGGCAAGGGCCTGGAGTG
GGTGGCCTCTATCTACTCCTATTCTGGCAGCACCTACTATGCCGACAGCG
TGAAGGGCCGGTTTACAATCAGCGCCGATACCTCCAAGAACACAGCCTAT
CTGCAGATGAATTCCCTGAGGGCAGAGGACACCGCAGTGTACTATTGTGC
CAGATACGGCGCCATGGATTATTGGGGCCAGGGCACCCTGGTGACAGTGT
CCTCTTAATCTAGA

2B1,
SEQ ID NO: 89
GGATCCGACATCCAGATGACCCAGTCCCCAAGCTCCCTGAGCGCATCCGT
GGGCGATAGGGTGACCATCACATGCAGGGCATCTCAGAGCGTGTCTAGCG
CAGTGGCATGGTACCAGCAGAAGCCAGGCAAGGCCCCTAAGCTGCTGATC
TACAGCGCCTCCTCTCTGTATAGCGGCGTGCCATCCCGGTTCTCCGGCAG
CCGGAGCGGAACCGACTTTACCCTGACAATCAGCTCCCTGCAGCCCGAGG
ATTTCGCCACATACTATTGCCAGCAGTACTCCGGCTCTGGCCACTATCTG
ATCACCTTTGGCCAGGGCACAAAGGTGGAGATCAAGGGAGGAGGCTCTGG
AGGAGGCAGCGGAGGCGGCTCCGAGGTGCAGCTGGTGGAGTCCGGCGGCG
GCCTGGTGCAGCCTGGAGGCTCTCTGAGGCTGAGCTGTGCAGCATCCGGC
TTCAACATCTACTCTAGCTCCATGCACTGGGTGCGCCAGGCACCAGGCAA
GGGCCTGGAGTGGGTGGCCAGCATCTCTAGCTCCTCTAGCTACACCTCTT
ATGCCGACAGCGTGAAGGGCCGGTTTACAATCTCCGCCGATACCTCTAAG
AACACAGCCTATCTGCAGATGAATTCCCTGAGGGCAGAGGACACCGCAGT
GTACTATTGTGCCAGAGGCTACTGGTACTATTGGGCCTGGTGGGCCAGCG
CCATGGATTATTGGGGCCAGGGCACCCTGGTGACAGTGTCCTCTTAATCT
AGA

2D9, SEQ ID NO: 90
GGATCCGACATCCAGATGACCCAGAGCCCAAGCTCCCTGAGCGCATCCGT
GGGCGATAGGGTGACCATCACATGCAGGGCATCTCAGAGCGTGTCTAGCG
CAGTGGCATGGTACCAGCAGAAGCCAGGCAAGGCCCCTAAGCTGCTGATC
TACAGCGCCTCCTCTCTGTATTCCGGAGTGCCTTCTCGGTTCTCCGGCAG
CCGGAGCGGAACCGACTTTACCCTGACAATCAGCTCCCTGCAGCCAGAGG
ATTTCGCCACATACTATTGCCAGCAGTGGTCCCACTATCTGATCACCTTT
GGCCAGGGCACAAAGGTGGAGATCAAGGGAGGAGGCAGCGGAGGAGGCTC

-continued

CGGAGGCGGCTCTGAGGTGCAGCTGGTGGAGTCCGGAGGAGGACTGGTGC

AGCCTGGAGGCAGCCTGAGGCTGTCCTGTGCAGCATCTGGCTTCAACCTG

TACTATTACTCTATGCACTGGGTGCGCCAGGCACCAGGCAAGGGCCTGGA

GTGGGTGGCCTCCATCTCTCCCAGCTACGGCTATACCAGCTACGCCGACT

CCGTGAAGGGCCGGTTCACAATCTCTGCCGATACCAGCAAGAACACAGCC

TATCTGCAGATGAATTCCCTGCGGGCCGAGGACACCGCCGTGTATTACTG

TGCCAGATCTAGCTTTTATTACTATGCCCTGGATTACTGGGGCCAGGGAA

CCCTGGTGACAGTGTCCTCTTAATCTAGA.

Cloning and Procedures for in Cell Expression—

The characterized mAbs were cloned to mammalian expression vectors (pCDNA3.1 or pMSCV PIG: Puro IRES GFP) in a reduced Fab form constructed by linear two copies of single chain variable Fragments (scFv) to ensure proper folding and expression. pCDNA3.1 is available from Addgene (Cambridge, Mass.) and GenScript (Piscataway, N.J.) used it to clone the Fab sequences. Memorial Sloan Kettering Cancer Center (New York, N.Y.) subcloned the Fab sequences from pCDNA3.1 to pMSCV. To easily detect the expression of Fabs and use them in pull-down experiments, 6 Myc tag sequences were included as an N-terminal tag to each scFv sequence during the cloning process. Transient expression of five Fabs in Mouse Embryo Fibroblasts (MEF) demonstrated that all Fabs are well expressed at similar levels. For more efficient transfection, Fab plasmids were transduced with retroviral transfection and stable Fab-expressing clones were selected using GFP as a selection marker. Co-immunoprecipitation experiments using anti-myc agarose beads pulled down the Fabs and demonstrated their capacity to bind BAX in cells using anti-BAX Western analysis.

Direct Binding ELISAs—

BAX (1 μg per well) was first immobilized on 96-well EIA/RIA plate (Corning Incorporated, Corning, N.Y.) at room temperature for 1 h or at 4° C. for overnight PBS containing 3% BSA was used to block the wells after BAX immobilization (incubation for 1.5 h at room temperature). The Fabs were diluted into PBS buffer (pH 7.0), applied to the wells, and incubated for 1 h at room temperature. The plates were then washed with PBS and incubated for 1 h with horseradish peroxidase/anti-FLAG M2 antibody conjugate (binding to the FLAG tag at the C-terminus of Fab light chain). The wells were washed with PBS, developed with 3,3',5,5'-tetramethylbenzidine (TMB) substrate, and quenched with 0.5 M $H_2SO_4$. The absorbance at 450 nm was determined. The data were fit to a standard four parameter logistic equation by using GraphPad Prism (GraphPad Software, La Jolla, Calif.). The half-maximal binding ($EC_{50}$) values were obtained from the inflection point of the curve.

Competitive Binding ELISAs—

Six Fab clones (3H1, 3G11, 3E8, 2A5, 2D9 and 2B1) were chosen for the competition ELISAs. Two different approaches were used. In the first approach, non-biotinylated Fabs were used to compete with the binding of biotinylated 3G11 (b3G11). To immobilized BAX on the 96-well EIA/RIA plate (Corning Incorporated, Corning, N.Y.), a mixture of 50 nM b3G11 and increasing amount of each of the six selected Fabs were added. After washes, only the binding of b3G11 was monitored using horseradish peroxidase/streptavidin conjugate and TMB substrate. In the second approach, purified Fab proteins were used to compete with Fabs displayed at the phage surface. Similarly, to immobilized BAX on the 96-well EIA/RIA plate (Corning Incorporated, Corning, N.Y.), a mixture of Fab-displayed phage (with a titer of ~1012 pfu/mL) and 100 nM of each of the six selected Fab proteins were added. Only the binding of Fab-phage complex binding was monitored using horseradish peroxidase/anti-M13 antibody conjugate and TMB substrate.

Biolayer Interferometry—

The forteBio BLItz system (Pall Corporation, Menlo Park, Calif.) was used to determine the binding kinetics and affinity between BAX and Fab proteins. Ni-NTA biosensors (Pall Corporation, Menlo Park, Calif.) were used for initial Fab protein immobilization, which was followed by BAX association and dissociation interaction analysis. 10 μg/mL Fab was used for immobilizing at pH 7. For each Fab protein, at least three different BAX concentrations, varying from 30 nM to 1.2 μM, were used, and subsequently global fitting was used to generate the ka (association rate constant), kd (dissociation rate constant) and KD (equilibrium dissociation constant) values.

Size-Exclusion Chromatography—

Superdex 75 10/300 GL and 200 10/300 GL (GE Healthcare) columns were used for size exclusion chromatography of recombinant BAX and Fab-BAX complex. Proteins were injected in columns equilibrated with a buffer containing 20 mM HEPES pH 7.2, and 150 mM KCl.

Liposome Permeabilization Assay—

Liposomes were composed of the following molar percentages of lipids (Avanti Polar Lipids): phosphatidylcholine, 48%; phosphatidylinositol, 10%; phosphatidylethanolamine, 28%; dioleoyl phosphatidylserine, 10%; and tetraoleoyl cardiolipin, 4% and were loaded with ANTS/DPX (Molecular Probe) upon extrusion. Fabs at the indicated concentrations in 96-well format (Corning), with and without BAX (400 nM) or BAX (400 nM) and tBID (30 nM) and then liposomes were added (10 μL from 1 mL lipid stock) in assay buffer (10 mM HEPES, pH 7, 200 mM KCl, and 1 mM $MgCl_2$) to a final volume of 100 μl. ANTS/DPX release was quantified based on the increase in fluorescence intensity that occurs when the ANTS fluorophore is separated from the DPX quencher upon release from the liposomes into solution. Fluorescence ($\lambda$ex=355 nm and $\lambda$em=520 nM) was measured over time at 30° C. using a Tecan Infinite M1000 plate reader. The percentage release of ANTS/DPX at 90 min was calculated as percentage release= ((F−F0)/(F100−F0))×100, where F0 and F100 are baseline and maximal fluorescence, respectively. 1% Triton treatment is used to determine the maximum amount of liposomal release per assay, and this value sets the 100% value for the kinetic curve figures whereas the calculated percent release value for the bar graphs was calculated by using the percent release value of tBid-induced BAX mediated ANT/DPX release as 100%.

BAX Translocation Assay—

Mitochondria from liver of $Bak^{-/-}$ mice (0.75 mg/ml) were resuspended in experimental buffer (125 mM KCl, 10 mM Tris-MOPS [pH 7.4], 5 mM glutamate, 2.5 mM malate, 1 mM $KPO_4$, 0.1 mM EGTA-Tris [pH 7.4]) and treated with the indicated concentrations of 3G11 recombinant BAX (200 nM) and tBid (100 nM), singly and in combination, and incubated at room temperature for 20 min. The supernatant fractions were isolated by centrifugation at 5500×g for 10 min and the mitochondrial pellets resuspended and washed with 0.1M sodium carbonate (pH 11.5) for 20 min, centrifuged at 13,000×g for 10 min at 4° C., and then solubilized in 1% Triton X-100/PBS for 1 h at 4° C. Mitochondrial supernatant and pellet fractions were separated by 4-12% NuPage (Invitrogen) gels and analyzed by immunoblotting with anti-BAX antibody (Cell Signaling Cat. 2772).

Mitochondrial Release Assay—

Mitochondria from liver of Bak$^{-/-}$ mice (1.5 mg/ml) were resuspended in experimental buffer (125 mM KCl, 10 mM Tris-MOPS [pH 7.4], 5 mM glutamate, 2.5 mM malate, 1 mM KPO$_4$, 0.1 mM EGTA-Tris [pH 7.4]) and treated with the indicated concentrations of 3G11 recombinant BAX (400 nM) and tBid (30 nM), singly and in combination, and incubated at room temperature for 60 min. The supernatants were isolated by centrifugation at 5500×g for 10 min and the mitochondrial pellets solubilized in 1% Triton X-100/PBS. Mitochondrial supernatant and pellet fractions were separated by 4-12% NuPage (Invitrogen) gels and analyzed by immunoblotting with anti-cytochrome c antibody (BD Biosciences Cat. 556433).

Western Blotting—

Samples from the mitochondria and translocation assay were electrophoretically separated on 4-12% NuPage (Invitrogen) gels, transferred to mobilon-FL PVDF membranes (Millipore) and subjected to immunoblotting. For visualization of proteins with Odyssey Infrared Imaging System (LI-COR Biosciences) membranes were blocked in PBS containing 3% milk powder. Primary BAX antibody (Cell Signaling 2772S) was incubated overnight at 4° C. in a 1:1,000 dilution. After washing, membranes were incubated with an IRdye800-conjugated goat anti-rabbit IgG secondary antibody (LI-COR Biosciences) in a 1:10,000 dilution. Proteins were detected with Odyssey Infrared Imaging System.

NMR Samples and Spectroscopy—

Uniformly 15N-labeled full-length human BAX was generated as previously described. Protein samples of BAX and BAX-3G11 mixtures at indicated concentrations were prepared in 25 mM sodium phosphate, 50 mM NaCl solution at pH 6.0 in 5% D20. Correlation 1H-15N HSQC and 1H-15N TROSY spectra were acquired at 25° C. on a Bruker 600 MHz NMR spectrometer equipped with a cryogenic probe, processed using Topsin, and analyzed with CCPNMR. BAX wild type cross-peak assignments were applied as previously reported (9).

Hydrogen/Deuterium Exchange Mass Spectrometry—

Prior to hydrogen-deuterium exchange experiments, the quench condition for best sequence coverage of BAX was optimized as previously described (28). Briefly, 3 µl of stock solution of BAX at 1.0 mg/ml was mixed with 9 µl of H$_2$O buffer (8.3 mM Tris, 150 mM NaCl, in H2O, pH7.2) at 0° C. and then quenched with 18 µl of ice cold quench solutions of 0.8% formic acid, 16% Glycerol, and GdnHCl at final concentrations of 0.05 M, 0.5 M, 1.0 M and 2.0 M. The quenched samples were frozen on dry ice and then subjected to an immobilized pepsin column (1×20 mm, 30 mg/ml porcine pepsin (Sigma)) for online digestion for 40 sec. The resulting peptides were collected on a C18 trap (Michrom MAGIC C18AQ 0.2×2) and separated using a reversed phase C18 column (Michrom MAGIC C18AQ 0.2×50 3 um 200 Å) with a 30 min linear gradient of 0.046% (v/v) trifluoroacetic acid, 6.4% (v/v) acetonitrile to 0.03% (v/v) trifluoroacetic acid, 38.4% (v/v) acetonitrile. The effluent was directed into an OrbiTtrap Elite mass spectrometer (Thermo-Fisher Sci. Inc) for MS analysis. The instrument was operated in positive ESI mode and the resolution of the instrument was set at 60,000. Proteome Discoverer software (Thermo Fisher Sci. Inc.) was used to identify the sequence of the resulting peptides. The optimal quench condition with the best coverage map of BAX (0.08M GuHCl in 0.8% formic acid) was used for subsequent functionally deuterated studies. Hydrogen-deuterium exchange reactions were initiated by diluting 3 µl of pre-chilled protein stock solution (free BAX, 1 mg/ml, or antibody-bound BAX, 2 mg/ml) into 9 µl D2O buffer (8.3 mM Tris, 150 mM NaCl, in D2O, pDREAD 7.2). The samples were incubated at 0° C. for 10 sec, 100 sec and 1000 sec. The exchange reaction was terminated by the addition of 18 µl of optimized quench solution at 0° C. and samples were immediately frozen on dry ice and stored at −80° C. In addition, un-deuterated samples and equilibrium-deuterated control samples were also prepared as previously described (29). The deuterated samples were then loaded onto above instrument for DXMS analysis. The centroids of the isotopic envelopes of un-deuterated, functionally deuterated, and equilibrium deuterated peptides were measured using HDExaminer, and then converted to corresponding deuteration levels with corrections for back-exchange (30).

Structure Calculations—

Structure calculations were performed with Crystallography and NMR system solve (CNS) within the HADDOCK web server using the prediction interface (31). HADDOCK calculations generated models of the complex that are in agreement with experimental distance restraints and have optimal electrostatic and van der Waals interactions based on a combination of molecular dynamics and energy minimization. HADDOCK docking was performed using the BAX NMR structural ensemble imported directly from the PDB (PDB ID: 1F16). The 3G11 structural model was generated using PIGS software based on structural homology modeling of known Fab structures of the same family that have different amino acid composition of CDR regions (32). Calculations were performed with ambiguous interaction restraints (AIR) derived from the hydrogen deuterium exchange mass spectrometry data and residues of the CDR regions of 3G11. For BAX AIR calculations, only residues that exhibited significant protection of hydrogen deuterium exchange upon titration and solvent accessibility over 50% as determined by the program NACCESS (Hubbard and Thornton, 1993) were defined as active residues; passive residues were automatically assigned by the HADDOCK web interface as those residues surrounding the active residues. For 3G11, AIR restraints were assigned based on residues involved in the CDRH1, CDRH2, CDRH3, and CDRL3. Specifically, active residues for BAX included residues 19-25 and 123-142; active residues for 3G11 were defined as Heavy Chain: 26-32 (Loop 1), 52-54 (Loop 2), 96-101 (loop 3) and Light Chain; 141-148, 165-168, and 206-211. In each HADDOCK structure calculation, 1000 orientations/structures of the complex were generated by rigid-body docking energy minimization of the individual structures. The 188 lowest energy structures were semi-flexibly refined in torsion angle space and then refined in explicit solvent. 132 structures formed the most populous cluster (HADDOCK score=−140.5±12.1 and Z-score=−1.7) with RMSD from the overall lowest energy structure (1.9±1.1 Å) calculated on the backbone (CA, C, N, O, P) atoms of all residues involved in intermolecular contact using a 10 Å cut-off. In all cases 3G11 was localized to N-terminal trigger site. Ribbon diagrams and molecular models were depicted using PYMOL (Schrodinger).

Results

Discovery of 14 Novel Synthetic Antibodies Targeting Monomeric BAX—

A restricted diversity phage antigen-binding fragment (Fab) library ("Library F") was used to select a panel of Fabs that bind to monomeric BAX (9). Library F was designed to contain mostly binomial Tyr/Ser diversity in CDR-H1 and H2, and expanded diversity, encoding the nine amino acids Tyr/Ser/Gly/Ala/Phe/Trp/His/Pro/Val in a 5/4/412/1/1/1/1/1 ratio, at CDR-L3 and H3 (33). In addition, the CDR-L3 and H3 loops vary in size. The expanded diversity in CDR-L3 and H3 in Library F was designed to mimic the distribution of amino acids in functional CDR-H3 segments of natural antibodies. Library F was screened against the monomeric BAX, which that was purified after utilizing chitin-column affinity purification and size exclusion chromatography (10). After 2-3 rounds of stringent selection, a panel of 14 BAX-specific Fabs with diverse CDR sequences was obtained (FIG. 1A). These clones were isolated from two distinct panning regimes, one in which biotinylated BAX was immobilized onto streptavidin-coated wells, and another in which BAX was coated directly on the wells. The properties of the selected clones were similar from either screening regime and thus further analyzed as a single conglomerated panel. Sequence comparison between the 14 Fabs revealed high diversity of residues and loop sizes in many positions with no apparent sequence homology in CDR segments from any two clones, demonstrating the diverse modes of interaction with BAX.

Fabs were expressed and purified and the half-maximal binding titers ($EC_{50}$) for BAX using ELISA were determined. The $EC_{50}$ values ranged from high affinity 2.3 nM (2B1) to moderate affinity 250 nM (2A5) with most Fabs having single or double digit nM nanomolar $EC_{50}$ (FIG. 1A). Select Fabs 3G11, 3E8, 2A5 and 2B1 were evaluated for binding kinetics to monomeric BAX using Biolayer Interferometry (FIG. 1B). The binding affinities ($K_D$ values) and ranking of the Fab proteins based on binding correlate with the $EC_{50}$ from ELISA. In both assays, Fabs 3G11, 3E8 and 2B1 were the highest-affinity binders to BAX, while Fab 2A5 was the lowest-affinity binder (FIG. 1A, 1B). Hence, an array of 14 high-affinity antibodies against monomeric BAX was identified.

Figure 1D:
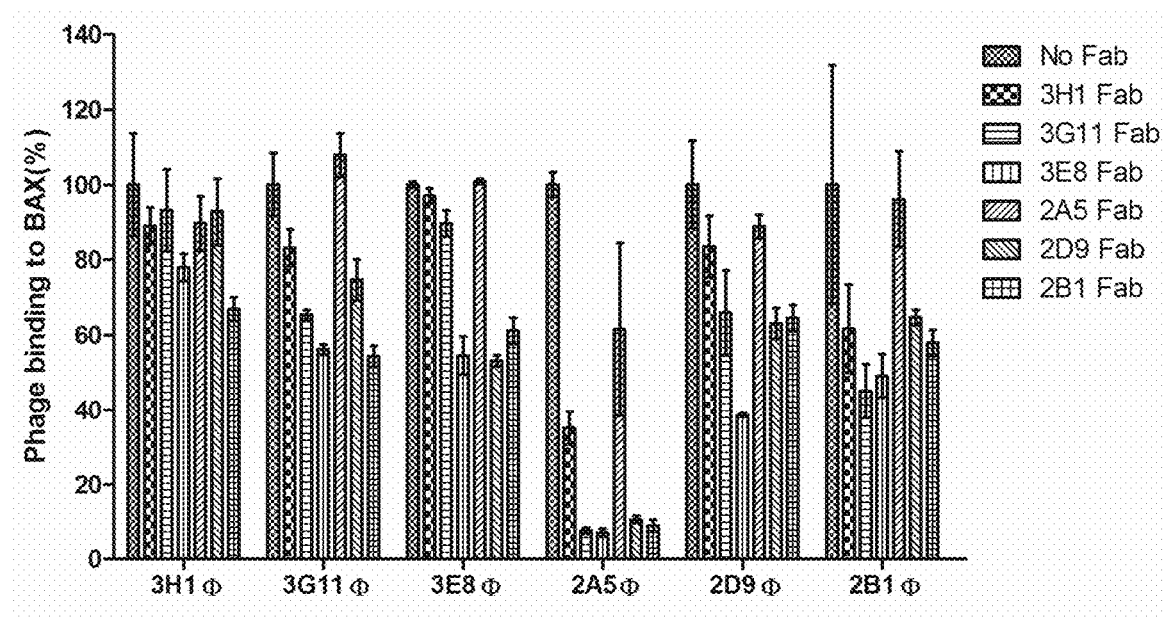

To explore if the Fabs engaged overlapping or distinct epitopes on BAX, competitive ELISA was performed using six of the clones (3H1, 3G11, 3E8, 2A5, 2D9 and 2B1) whose $EC_{50}$ values cover the entire affinity range. A competitive ELISA was performed in which Fab 3G11 was first biotinylated (b3G11) and binding of b3G11 to BAX in the presence of other non-biotinylated Fab proteins was analyzed. All Fabs except Fab 2A5 demonstrated competitive inhibition of b3G11 binding with $IC_{50}$s ranging from nM to μM (FIG. 1C). Fab 2A5 does not compete b3G11 binding likely because it is a much weaker binder than 3G11. Furthermore, a study was also conducted of how binding of phage-expressed Fabs (Φ) can be competitively inhibited by free Fab proteins. The data showed that phage-expressed Fab binding was inhibited to varying degrees in the presence of 100 nM Fab protein for many of the clones and that, in each case, the phage-expressed Fab for a particular clone could be inhibited by its own Fab protein (FIG. 1D). Again, Fab 2A5, the lowest affinity clone ($EC_{50}$=250 nM) had little effect on Fab phage binding for all the other clones, but all the other Fabs proteins could significantly inhibit Fab 2A5 phage binding. On the contrary, Fabs 3E8 and 2B1, the highest affinity clones ($EC_{50}$s=2.6 nM and 2.3 nM, respectively) showed the strongest inhibition on all Fab phage binding. Therefore, the competitive ELISA data matches predictions based on ELISA half-maximal binding titers and $K_D$ values. These results indicate that, to a large extent, these Fabs have overlapping epitopes on the BAX surface with a range of affinities, but many in the low nanomolar range.

Synthetic Antibodies Inhibit BH3-Triggered BAX Activation and MOMP—

Figure 2A:
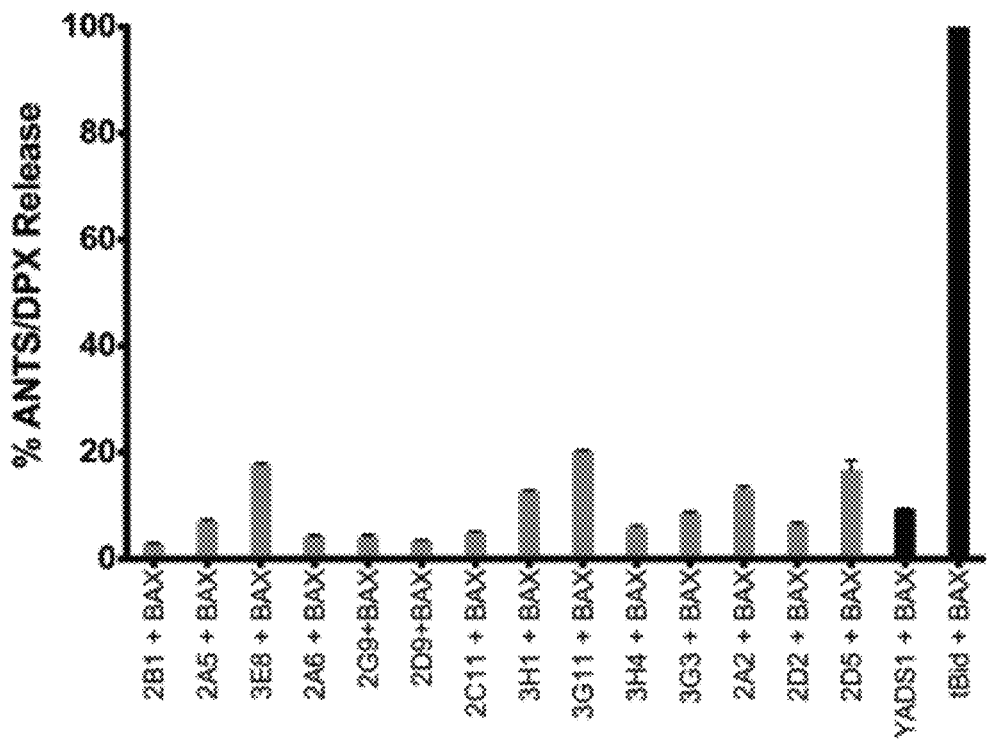
FIG. 2A-2F. Synthetic Fabs inhibit BAX activation induced by pro-apoptotic tBID in liposomal assay. (A) Synthetic BAX-binding Fabs or a VEGF specific Fab (YADS1) at 2 μM have no capacity to induce BAX-mediated liposomal ANT/DPX release while tBID induced potent BAX-mediated liposomal release. (B) BAX-binding Fabs at 2 µM, except 2A5 and YADS1, inhibit tBID-induced BAX-mediated liposomal ANT/DPX release. Bars represent mean±SD value at 90 min that is normalized to tBID-induced maximum ANTS/DPX release at 90 min (C-F). Representative liposomal ANTS/DPX release experiments in kinetic representation showing the inhibitory activity of Fabs 3G11, 2B1 and 3E8 at 0.5 µM, 1 µM and 2 µM Fab whereas 2A5 had no inhibitory effect. Experiments performed with 400 nM BAX, 30 nM tBID and up to 2 µM Fabs (A-F). Data shown in (A-F) represent mean±SD from triplicates normalized using either tBid-induced BAX mediated ANTS/DPX release as 100% (A-B) or 1% triton release as 100% (C-F). Data shown are representative of at least three independent experiments.
Figure 2B:
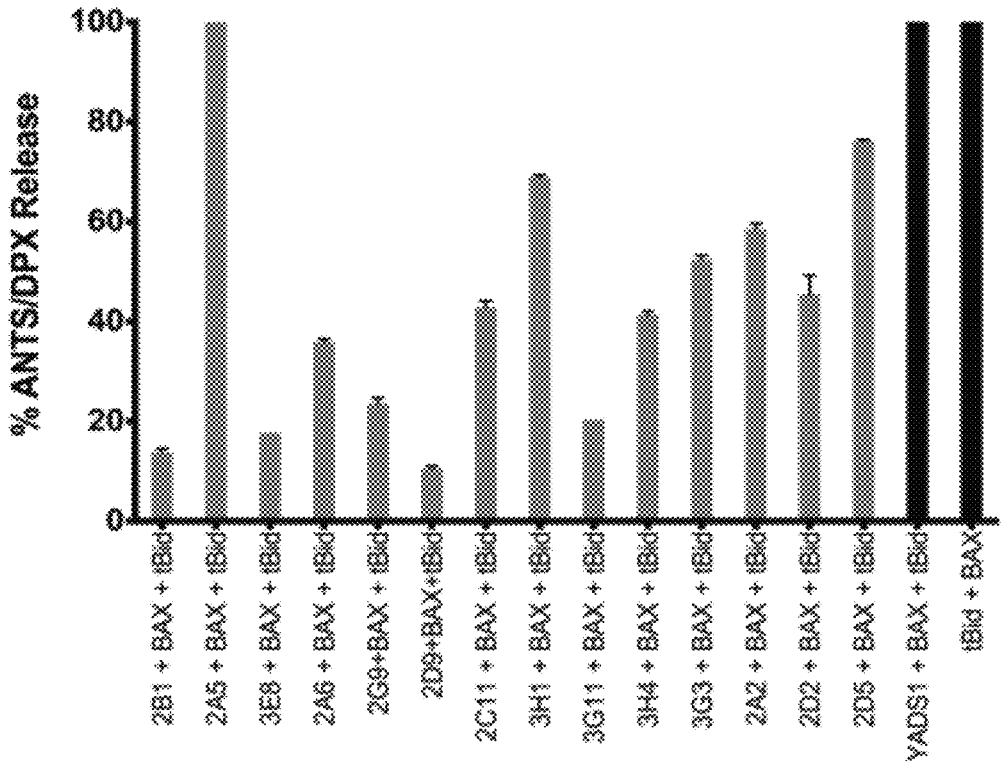
Figure 2C:
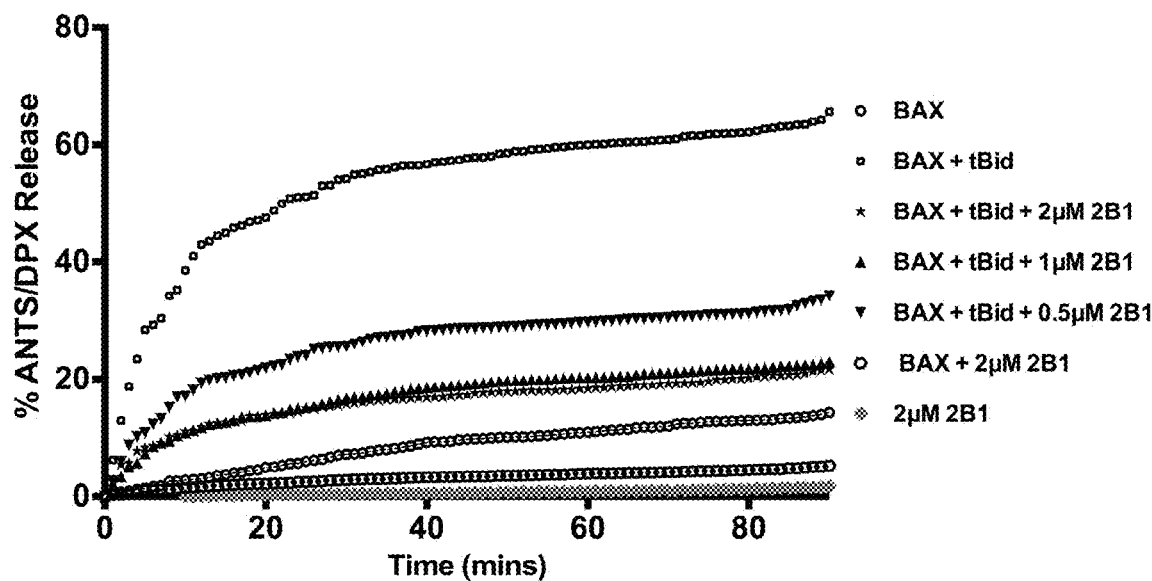
Figure 2D:
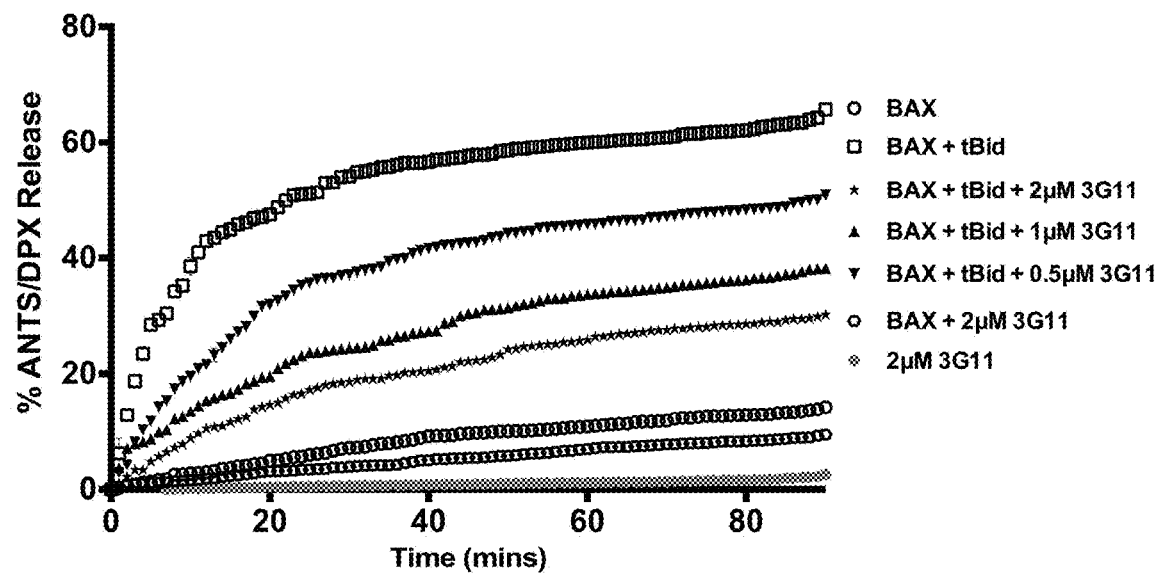
Figure 2E:
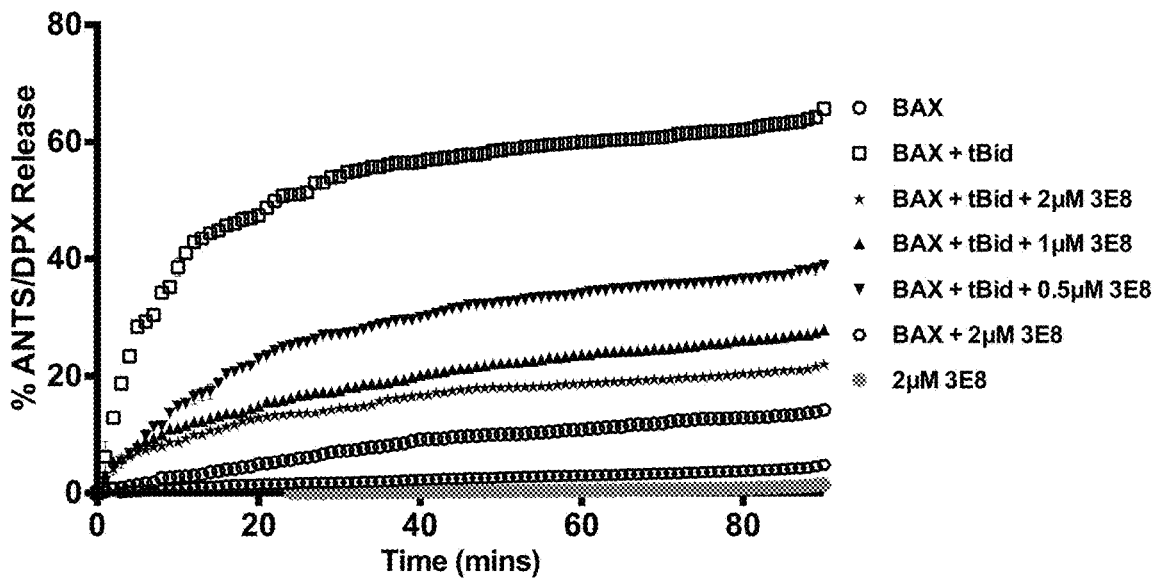
Figure 2F:
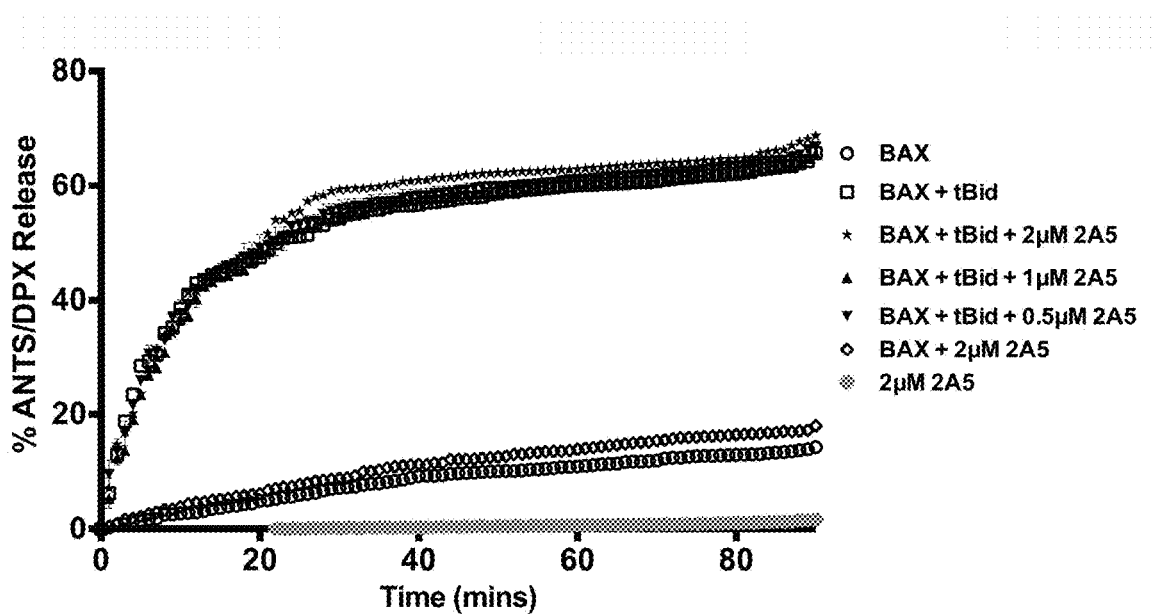

To examine how binding to BAX by Fabs proteins modulates BAX function, liposomal assays were performed that explicitly evaluate how BH3-triggered BAX forms a pore in a membrane environment made from similar lipid composition of mitochondria without the contribution of other mitochondrial factors (34). Selected Fabs have the potential to activate BAX by engaging one of the activation sites of BAX either at its N-terminal or C-terminal surface (10, 15, 35, 36) or inhibit BAX activation by inhibiting the BAX binding surface of the activator protein tBID or conformational changes associated with BAX activation (12, 15, 16, 20, 37). Therefore, the capacity of the Fabs to either activate BAX or inhibit BAX activation induced by tBID was examined. None of the 14 Fabs had an effect on the liposomal integrity alone; neither does an unrelated vascular-endothelial growth factor (VEGF)-specific Fab (YADS1, negative control). Furthermore, none of the Fab proteins activated BAX and induced liposomal release (FIG. 2A). However, when tBID and BAX are combined with liposomes, liposomal release is robust as expected (FIG. 2A, 2B). In contrast, high affinity Fabs when combined with tBID and BAX inhibited tBID-triggered BAX activation significantly, or completely, at 2 μM, in all cases, except with the exception of the lower affinity clone Fab 2A5 and the negative control YADS1 (FIG. 2B). Three of the highest binding Fabs 3G11, 3E8 and 2B1 yielded dose-responsive and time-dependent inhibition of liposomal release whereas the weaker binder 2A5 had no effect even at 2 μM (FIG. 2C-2F).

Figure 3A:
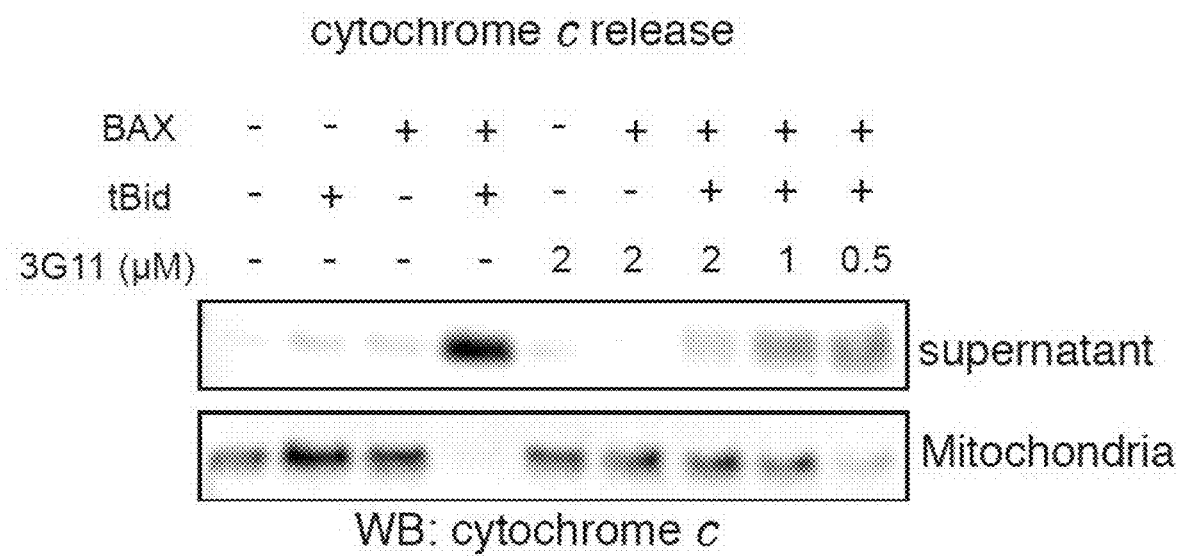
FIG. 3A-3B. Synthetic Fab 3G11 inhibit BAX-mediated cytochrome c release and BAX mitochondrial translocation induced by pro-apoptotic tBID in isolated mitochondria. (A) Fab 3G11 inhibits dose-responsively tBID-induced BAX-mediated cytochrome c release from isolated BAK$^{-/-}$ mitochondria. (B) 3G11 Fab inhibits dose-responsively tBID-induced BAX mitochondrial translocation in isolated BAK$^{-/-}$ mitochondria. Data shown are representative of at least three independent experiments.
Figure 3B:
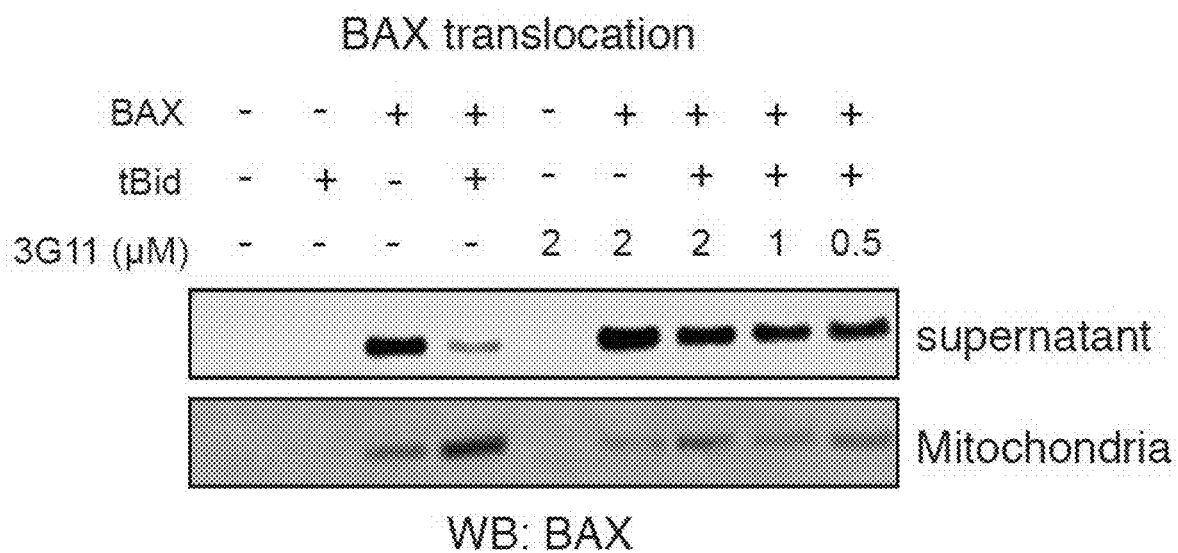

To examine whether Fabs can inhibit BAX activation in the presence of mitochondrial membranes loaded with anti-apoptotic BCl-2 or other mitochondrial proteins, mouse liver mitochondria were isolated from Bak$^{-/-}$ mice to perform a mitochondrial release assay. Combination of tBID and BAX was exposed to several doses of Fab 3G11, which demonstrated dose-responsive inhibition of mitochondrial cytochrome c release induced by activated BAX, as assessed by separation of the supernatant and mitochondrial fractions and western analysis (FIG. 3A). Moreover, using the mitochondria assay, BAX localization was determined to examine whether inhibition by Fab 3G11 was due to prevention of BAX translocation to the membrane or blocking of the membrane integration and oligomerization on the outer mitochondrial membrane. Fab 3G11 dose-responsively inhibited the capacity of BAX for mitochondrial translocation suggesting that 3G11's high affinity binding to the monomeric BAX either competes binding of tBID or prevents conformational changes of BAX required for its mitochondrial translocation (FIG. 3B). Taken together, these data indicate that these Fab proteins inhibit BH3-triggered BAX activation and MOMP by restraining mitochondrial membrane translocation of BAX.

Fab 3G11 Protein Forms a Stable and Stoichiometric Complex with BAX—

To investigate the effect of synthetic Fab proteins on the structure of BAX, the stability and stoichiometry of several Fab-BAX complexes were studied upon mixing the protein at various concentrations and analyzing by size-exclusion chromatography (SEC) (data not shown). Based on gel SEC and SDS-PAGE analysis, binding of the Fab 3G11 to BAX results in a stable 1:1 stoichiometric complex. 3G11 was selected for further structural analysis because of its high affinity and low dissociation constant (FIG. 1B). Next, structural effects of the 3G111 were analyzed based on 1H-15N HSQC spectra of full length BAX monomer at several doses of 3G11. The HSQC spectra are in agreement with the 3G11 and BAX forming a stable complex, with a 1:1 stoichiometry and in slow exchange on the NMR time scale as evidenced by the dose-dependent loss of intensity of the cross peaks of the monomeric BAX and lack of new chemical shifts upon 3G11 titration. Despite the 3G11-BAX complex formation evidenced by the NMR titration, it is not possible to observe the $^1$H-$^{15}$N cross peaks of the complex in the $^1$H-$^{15}$N HSQC spectra due to the size of the complex (70 KDa).

Fab 3G11 Protein Binds the N-terminal Surface of BAX to Prevent BAX Activation

To further analyze the Fab-BAX interaction, the changes on the BAX structure were analyzed by measuring the solvent accessibility and hydrogen-deuterium exchange of the backbone amide hydrogens using hydrogen-deuterium exchange mass spectrometry (HXMS). First, the deuterium exchange of unbound BAX was analyzed in solution, which underlined the different deuterium exchange rates for exposed or unfolded regions (N-terminus, α1-α2 loop) and more solvent-protected or structured regions including α2, α3-α4, α5, α6-α8. Upon 3G11-BAX complex formation at stoichiometric levels, deuterium exchange, sample digestion, preparation and analysis was performed in the same conditions as with free BAX. Interestingly, HXMS analysis of the Fab-bound BAX in solution highlighted significant solvent protection in helix α1 and α6 and the α1-α2 loop while other regions of the BAX structure had little to no change in the deuterium incorporation upon interaction with the 3G11. Furthermore, HXMS showed a modest increase in solvent accessibility for residues in helices α7, α8 and partially α9 and α2 that are found at the C-terminal surface of BAX. Binding of the 3G11 Fab to full-length BAX (BAX WT) and to the C-terminal helix α9-truncated BAX (BAX ΔC) was determined with similar dissociation constant $K_D$ (Table 1), suggesting that major contacts of 3G11 occur elsewhere from the C9 or the canonical hydrophobic groove of BAX.

Figure 4:
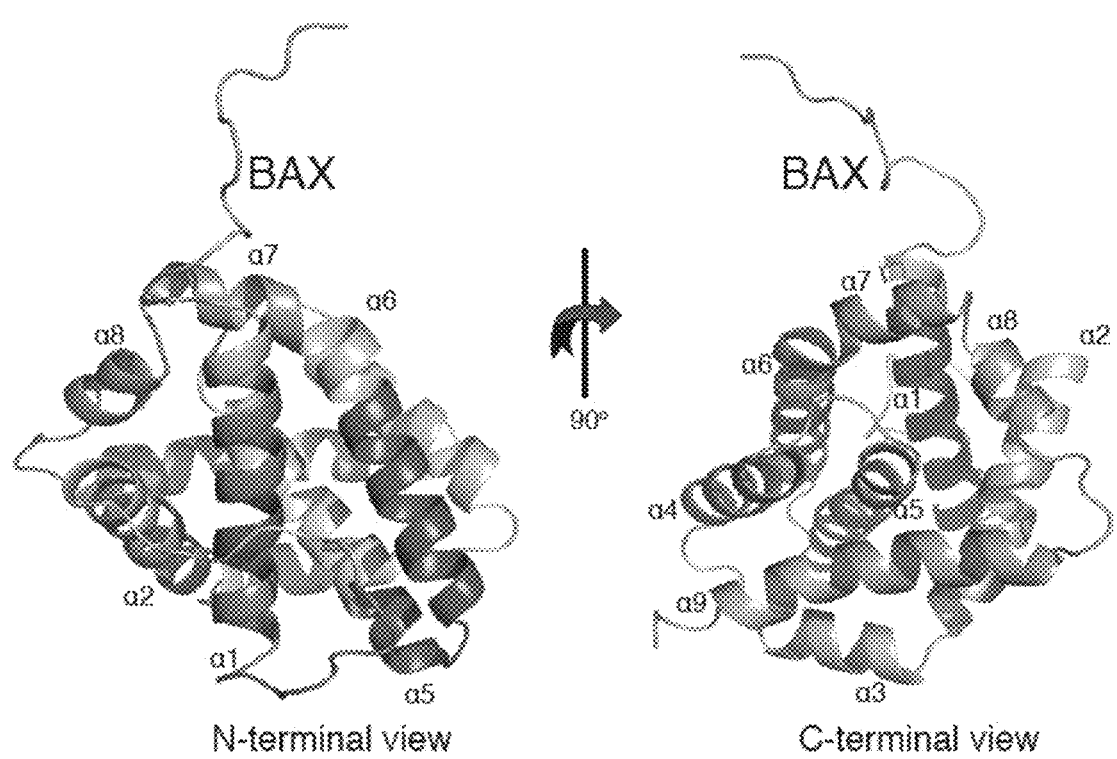
FIG. 4. 3G11 binds to the N-terminal surface of BAX. % deuterium incorporation of unbound BAX conformation was determined in solution. HXMS analysis suggests increased rates of deuterium exchange in the N-terminal region of BAX, the α1-α2 loop and helices α2, part of α5, α8, and α9. The relative difference of % deuterium incorporation of BAX conformation bound to 3G11 minus the % deuterium incorporation of BAX conformation alone was also determined. HXMS analysis suggests increased protection from deuterium incorporation in residues of helices α1, α6, part of α5 and the α1-α2 loop compared to the unbound BAX. The regions of significant protection from deuterium incorporation (>–20%) are highlighted in dark on the sequence of BAX (SEQ ID NO:57). The ribbon representation of the full length BAX structure (PDB ID: 16F6) is shown in the bottom portion of the figure.

The HXMS analysis suggests that the binding region of the 3G11 is localized on the N-terminal surface of the BAX structure and overlaps with the 1) N-terminal trigger site of BAX (α1/α6) that controls a series of conformational changes upon BH3 domain activation (11-12) and 2) the binding epitope (residues 12-24) that is recognized by the 6A7 antibody only on the conformational active BAX (FIG. 4). Interestingly, the α1-α2 loop, whose displacement was determined to be essential for the initiation of conformational changes upon BH3-triggered BAX activation (12), is protected by the Fab binding interaction. Thus, the binding interaction of 3G11 to BAX is localized to the N-terminal surface of BAX, overlapping with the N-terminal trigger site and preventing conformational changes that lead to activation of the monomeric BAX.

Although recent structural studies based on peptides from the cytomegalovirus protein vMIA (38) and BCL-2 (20) proteins suggested potential sites that intervene with BAX activation, interestingly, none of these peptides directly block the N-terminal activation site of the soluble BAX or the C-terminal activation site of the mitochondrial associated BAX. A protein-protein structure calculation approach (39) was used to further confirm this novel interaction of 3G11 bound to the N-terminal surface of BAX. HADDOCK structure calculations were performed using ambiguous interaction restraints between BAX residues determined by HXMS to be most protected from solvent upon 3G11 binding (residues of the α1, α6 and the α1-α2 loop) and residues of the CDR regions present in the 3G11 protein sequence. Furthermore, calculations included an NMR structural ensemble of BAX with different loop conformations. Based on these calculations, the 3G11 binds more favorably in a direct interaction with N-terminal trigger site of BAX and the closed conformation of α1-α2 loop (10, 12). 3G11 protein makes interactions of hydrophobic and hydrophilic nature with the solvent-exposed hydrophobic residues and polar/charged residues of the BAX trigger site covering a large interface surface of (1640 Å).

Figure 5A:
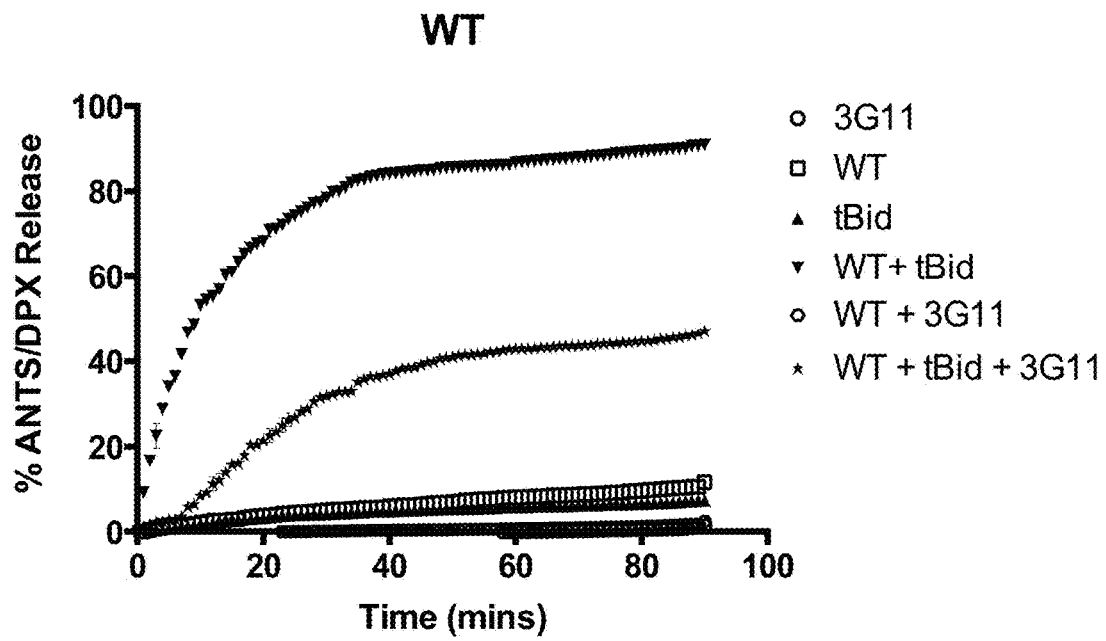
FIG. 5A-5F. Select BAX mutants inhibit functional inhibition and binding to BAX by 3G11. (A-D) Representative liposomal ANTS/DPX release experiments in kinetic representation showing the inhibitory activity of 3G11 (2 µM) with BAX WT that is weakened by the K21E mutation and completely abolished by the R134E or the double mutation R134E/K21E. Experiments performed with 400 nM BAX WT or BAX mutants, 30 nM tBID and 2 µM 3G11. (E) % Inhibition based on the maximum tBID-induced BAX activation for BAX WT and mutants at 90 min in presence or absence of 3G11 Fab. (F) ELISA binding profiles for 3G11 binding to BAX WT and mutants. Half-maximal binding titers (EC50) were determined as follows: 8±2 nM for BAX WT, 29±4 for K21E, 89±2 nM for R134E mutant and 91±2 nM for the R134E/K21E double mutant. Data shown in (A-D) represent mean±SD from triplicates and at least two independent experiments.
Figure 5B:
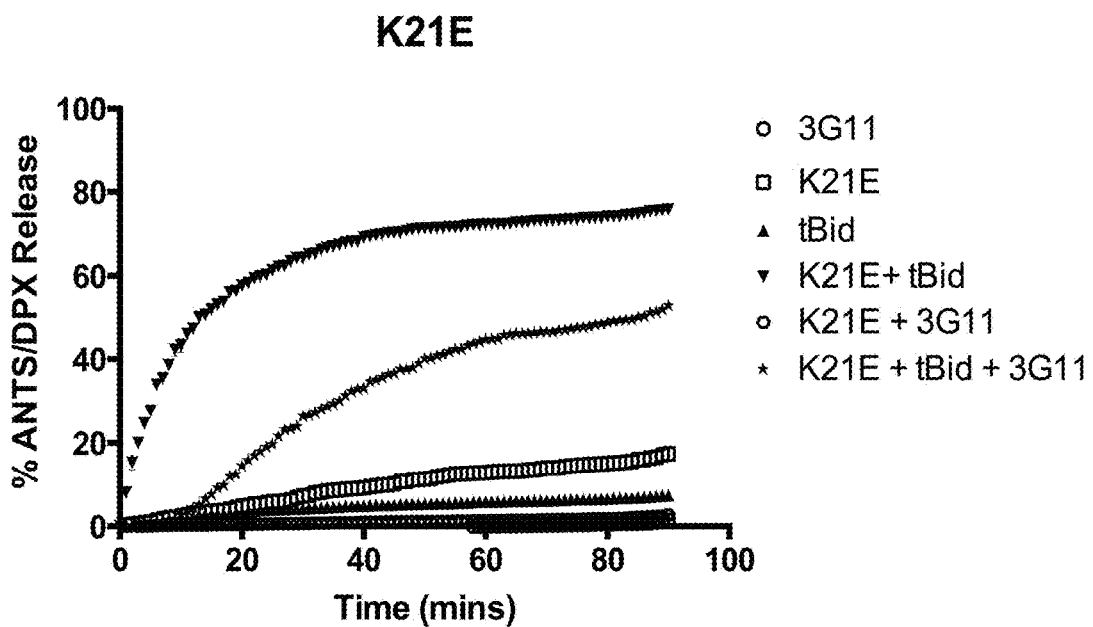
Figure 5C:
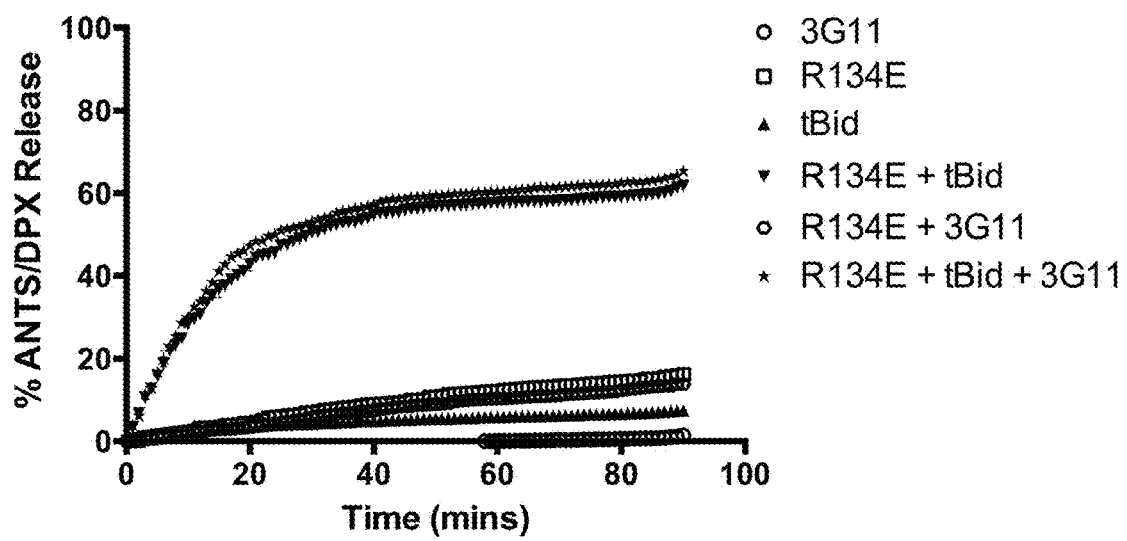
Figure 5D:
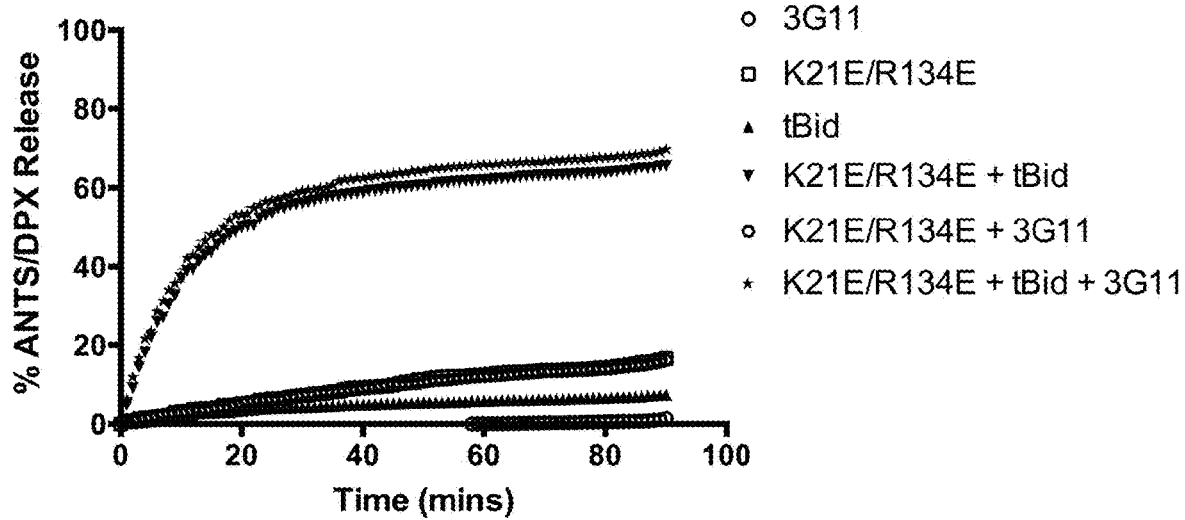
Figure 5E:
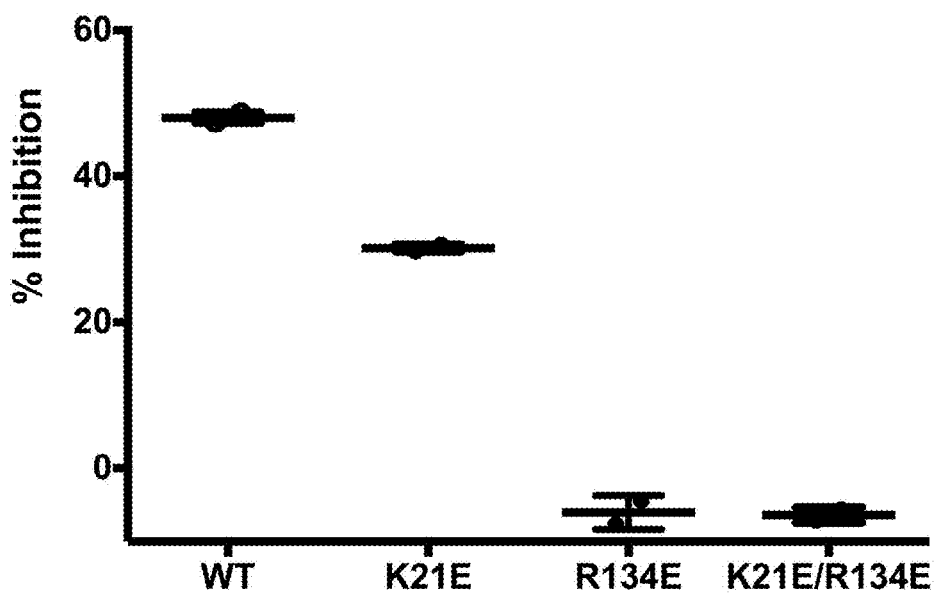
Figure 5F:
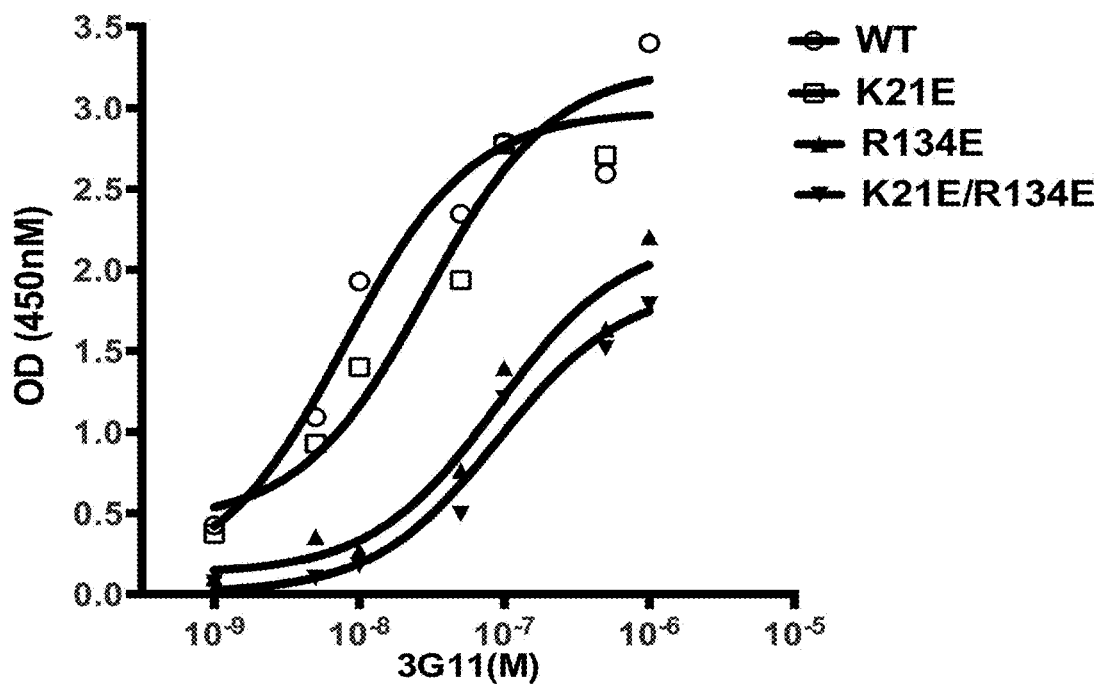

To validate the 3G11 direct interaction with the N-terminal trigger site, it was tested whether mutations on BAX can disrupt binding to 3G11 and affect its inhibitory activity of 3G11 in liposomal ANTS/DPX release assays. The 3G11-BAX structural model was used. Residues on BAX were selected that form contacts with residues of 3G11 using a 3 Å cutoff. Residues K21 in helix α1 and R134 in helix α6 have previously been shown to interact with the stapled BIM BH3 peptide that activates BAX through the N-terminal trigger site (10). Further analysis of the structural model showed that R134 residue forms hydrogen bonds with four residues (S30, Y31, Y32, S33) in 3G11 CDR-H1 loop while the K21 residue is predicted to form one hydrogen bond interaction with residue S143 in 3G11. Consistently with the predicted contributions of each residue to the interaction with 3G11 Fab, liposomal ANTS/DPX release experiments showed that the inhibition effect of 3G11 on BAX WT activation by tBID is weakened with the presence of the K21E mutation, but it is was completely abolished with the R134E mutation (FIG. 5A-5E). Likewise, the double mutation R134E/K21E also abolished the capacity of 3G11 to inhibit BAX activation (FIG. 5D, 5E). The inability of 3G11 to inhibit activation of these BAX mutants is consistent with the decreased affinity of 3G11 to these BAX mutants as determined by ELISA binding experiments (FIG. 5F). Thus, the data suggest that 3G11 binds and blocks access to the N-terminal trigger site of BAX and therefore directly prevents BAX activation and its associated conformational changes. In accordance, mapping the predicted BAX interacting residues based on the 3G11-BAX structural model and residues of the trigger site that interact with the stapled BIM BH3 peptide as determined by NMR studies demonstrates an extensive overlap (10). Taken together, these results suggest a novel mechanism of BAX inhibition and demonstrate the capacity of the reported Fabs as structural and functional probes of BAX.

Discussion

Decision of cellular life or death through the mitochondrial apoptotic pathway, in physiological or disease conditions, is mainly controlled by the interactions among the BCL1-2 family proteins. Activation of pro-apoptotic BAX is essential for apoptosis to proceed through mitochondrial dysfunction and caspases activation. Here, synthetic antibody technology was harnessed to generate high affinity BAX binding antibody fragments (Fabs). The screen identified at least 14 different Fabs with sequence diversity in CDR regions that bind with nM affinity to BAX. Interestingly, the competitive ELISAs confirmed that the identified Fab proteins bind to overlapping regions of the BAX surface. Selected Fabs bind full length BAX, which represents cytosolic BAX (9). It was demonstrated that 3G11 binds C-terminal truncated BAX, which mimics the mitochondrial-associated BAX (15). Mitochondrial inserted BAX oligomerizes and undergoes dramatic conformational changes of the monomeric BAX to such extent that the N-terminal surface of BAX is not available for binding to Fabs (13, 15, 16, 40). Therefore, selected Fabs are expected to be conformational specific for cytosolic and mitochondrial-associated BAX and inhibit both conformations from proceeding along the BAX activation process.

All of the identified BAX-binding Fabs inhibit BAX activation triggered by pro-apoptotic tBID in liposomal and mitochondrial assays. Further investigation of the mechanism, using Fab 3G11protein, indicated that the Fabs bind to the N-terminal surface of BAX without causing significant conformational changes on BAX. HADDOCK calculations and mutagenesis show that 3G11 binds to an extended surface on BAX that includes the N-terminal trigger site (helices α1/α6), which BIM, BID, and PUMA pro-apoptotic BH3 helices bind to trigger BAX activation (10, 11, 36, 38, 41). The data indicate that 3G11 competitively inhibits tBID-mediated BAX activation by blocking access to the N-terminal trigger site and preventing N-terminal conformational changes associated with BAX activation (11, 36). Indeed, 3G11-binding prevents mitochondrial translocation of BAX, which requires significant conformational changes and integration into the membrane (13, 15, 16, 40).

BAX is shown to have two different activation sites depending on its cytosolic or mitochondrial associated conformations; the N-terminal BH3 pocket (trigger site) and the C-terminal BH3 pocket Although several proteins have been reported to directly bind BAX and inhibit its activation, only two other studies reported structural evidence of the binding interaction on the surface of BAX. A stapled helical peptide of the BH4 domain of BCL-2 protein binds to a cleft formed by select residues of the α1-α2 loop, α2, 3, α5 and α6 (20). A helical peptide of the cytomegalovirus protein vMIA binds to a distinct site at the same side of the BAX structure that includes the loops of α3-α4 and α5-α6 (38). In both cases, the peptides bind to a geographically distinct site that have no overlap with either of the N-terminal or C-terminal activation site. Therefore, these mechanisms of BAX inhibition reflect allosteric mechanisms that suppress conformational changes upon BAX activation. The present data indicate that the direct inhibition mechanism of BAX by 3G11 Fab through interaction with the N-terminal activation site is a feasible and effective mechanism of BAX inhibition.

Pharmacological targeting of BAX whether to either promote or inhibit its activation has been proposed to be a promising therapeutic strategy. However, discovery of pharmacological modulators of BAX has been challenging due to limited insights or lack of appropriate probes to use for small molecule discovery. Recently, small molecule BAX activators that bind to the BAX trigger site have been identified using a competitive binding assay of the stapled BIM BH3 peptide activator that binds to the same site (42). Likewise, the application of synthetic antibodies to BAX provides a novel opportunity to use Fabs as probes for screening small molecule libraries using a competitive binding assay between the identified inhibitory Fabs and BAX. Such small molecule inhibitors that bind directly to the BAX trigger site will be effective for development of therapeutics.

TABLE 1

Binding kinetics and thermodynamics of Fab 3G11 with BAX WT and BAX ΔC.

| BAX | $k_{on}$ (M$^{-1}$ s$^{-1}$) | $k_{off}$ (s$^{-1}$) | $K_D$ (nM) |
|---|---|---|---|
| BAX WT | $(3.0 \pm 1.5) \times 10^5$ | $(1.1 \pm 0.1) \times 10^{-2}$ | $38 \pm 12$ |
| BAX ΔC | $(2.9 \pm 0.5) \times 10^5$ | $(1.8 \pm 0.1) \times 10^{-2}$ | $65 \pm 13$ |

REFERENCES

1. Fuchs, Y., and Steller, H. (2011) Programmed cell death in animal development and disease. Cell 147, 742-758
2. Danial, N. N., and Korsmeyer, S. J. (2004) Cell death: critical control points. Cell 116, 205-219
3. Youle, R. J., and Strasser, A. (2008) The BCL-2 protein family: opposing activities that mediate cell death. Nat. Rev. Mol. Cell Biol. 9, 47-59
4. Chipuk, J. E., Moldoveanu, T., Llambi, F., Parsons, M. J., and Green, D. R. (2010) The BCL-2 family reunion. Mol. Cell 37, 299-310
5. Hsu, Y. T., Wolter, K. G., and Youle, R. J. (1997) Cytosol-to-membrane redistribution of Bax and Bcl-X(L) during apoptosis. Proc. Nat. Acad. Sci. USA 94, 3668-3672
6. Wolter, K. G., Hsu, Y. T., Smith, C. L., Nechushtan, A, Xi, X. G., and Youle, R. J. (1997) Movement of Bax from the cytosol to mitochondria during apoptosis. J. Cell Biol. 139, 1281-1292
7. Walensky, L. D., and Gavathiotis, E. (2011) BAX unleashed: the biochemical transformation of an inactive cytosolic monomer into a toxic mitochondrial pore. Trends Bioch. Sci. 36, 642-652
8. Westphal, D., Kuck, R. M., and Dewson, G. (2014) Building blocks of the apoptotic pore: how Bax and Bak are activated and oligomerize during apoptosis. Cell Death Diff. 21, 196-205
9. Suzuki, M., Youle, R. J., and Tjandra, N. (2000) Structure of Bax: coregulation of dimer formation and intracellular localization. Cell 103, 645-654
10. Gavathiotis, E., Suzuki, M., Davis, M. L., Pitter, K., Bird, G. H., Katz, S. G., Tu, H. C., Kim, H., Cheng, E. H., Tjandra, N., and Walensky, L. D. (2008) BAX activation is initiated at a novel interaction site. Nature 455, 1076-1081
11. Kim, H., Tu, H. C., Ren, D., Takeuchi, O., Jeffers, J. R., Zambetti, G. P., Hsieh, J. J., and Cheng, E. H. (2009) Stepwise activation of BAX and BAK by tBID, BIM, and PUMA initiates mitochondrial apoptosis. Mol. Cell 36, 487-499
12. Gavathiotis, E., Reyna, D. E., Davis, M. L., Bird, G. H., and Walensky, L. D. (2010) BH3-triggered structural reorganization drives the activation of proapoptotic BAX. Mol. Cell 40, 481-492
13. Gahl, R. F., He, Y., Yu, S., and Tjandra, N. (2014) Conformational rearrangements in the pro-apoptotic protein, Bax, as it inserts into mitochondria: a cellular death switch. J. Biol. Chem. 289, 32871-32882
14. Lovell, J. F., Billen, L. P., Bindner, S., Shamas-Din, A., Fradin, C., Leber, B., and Andrews, D. W. (2008) Membrane binding by tBid initiates an ordered series of events culminating in membrane permeabilization by Bax. Cell 135, 1074-1084
15. Czabotar, P. E., Westphal, D., Dewson, G., Ma, S., Hockings, C., Fairlie, W. D., Lee, E. F., Yao, S., Robin, A. Y., Smith, B. J., Huang, D. C., Kluck, R. M., Adams, J. M., and Colman, P. M. (2013) Bax crystal structures reveal how BH3 domains activate Bax and nucleate its oligomerization to induce apoptosis. Cell 152, 519-531
16. Bleicken, S., Jeschke, G., Stegmueller, C., Salvador-Gallego, R., Garcia-Saez, A. J., and Bordignon, E. (2014) Structural model of active Bax at the membrane. Mol. Cell 56, 496-505
17. Sattler, M., Liang, H., Nettesheim, D., Meadows, R. P., Harlan, J. E., Eberstadt, M., Yoon, H. S., Shuker, S. B., Chang, B. S., Minn, A. J., Thompson, C. B., and Fesik, S.

W. (1997) Structure of Bcl-xL-Bak peptide complex: recognition between regulators of apoptosis. Science 275, 983-986

18. Ding, J., Zhang, Z., Roberts, G. J., Falcone, M., Miao, Y., Shao, Y., Zhang, X. C., Andrews, D. W., and Lin, J. (2010) Bcl-2 and Bax interact via the BH1-3 groove-BH3 motif interface and a novel interface involving the BH4 motif. J. Biol. Chem. 285, 28749-28763

19. Ding, K., Wang, H., Wu, Y., Zhang, L., Xu, J., Li, T., Ding, Y., Zhu, L., and He, J. (2015) Rapamycin protects against apoptotic neuronal death and improves neurologic function after traumatic brain injury in mice via modulation of the mTOR-p53-Bax axis. J. Surg. Res. 194, 239-247

20. Barclay, L. A., Wales, T. E., Garner, T. P., Wachter, F., Lee, S., Guerra, R. M., Stewart, M. L., Braun, C. R., Bird, G. H., Gavathiotis, E., Engen, J. R., and Walensky, L. D. (2015) Inhibition of Pro-apoptotic BAX by a noncanonical interaction mechanism. Mol. Cell 57, 873-886

21. Czabotar, P. E., Lessene, G., Strasser, A., and Adams, J. M. (2014) Control of apoptosis by the BCL-2 protein family: implications for physiology and therapy. Nat. Rev. Mol. Cell Biol. 15, 49-63

22. Sidhu, S. S., and Fellouse, F. A. (2006) Synthetic therapeutic antibodies. Nat. Chem. Biol. 2, 682-688

23. Paduch, M., Koide, A., Uysal, S., Rizk, S. S., Koide, S., and Kossiakoff, A. A. (2013) Generating conformation-specific synthetic antibodies to trap proteins in selected functional states. Methods 60, 3-14

24. Fellouse, F. A., Esaki, K., Birtalan, S., Raptis, D., Cancasci, V. J., Koide, A., Jhurani, P., Vasser, M., Wiesmann, C., Kossiakoff, A. A., Koide, S., and Sidhu, S. S. (2007) High-throughput generation of synthetic antibodies from highly functional minimalist phage-displayed libraries. J. Mol. Biol. 373, 924-940

25. Koellhoffer, J. F., Chen, G., Sandesara, R. G., Bale, S., Saphire, E. O., Chandran, K., Sidhu, S. S., and Lai, J. R. (2012) Two synthetic antibodies that recognize and neutralize distinct proteolytic forms of the ebola virus envelope glycoprotein. Chembiochem 13, 2549-2557

26. Koerber, J. T., Thomsen, N. D., Hannigan, B. T., Degrado, W. F., and Wells, J. A. (2013) Nature-inspired design of motif-specific antibody scaffolds. Nat. Biotech. 31, 916-921

27. Gao, J., Sidhu, S. S., and Wells, J. A. (2009) Two-state selection of conformation-specific antibodies. Proc. Nat. Acad. Sci. USA 106, 3071-3076

28. Marsh, J. J., Guan, H. S., Li, S., Chiles, P. G., Tran, D., and Morris, T. A. (2013) Structural insights into fibrinogen dynamics using amide hydrogen/deuterium exchange mass spectrometry. Biochem. 52, 5491-5502

29. Li, S., Tsalkova, T., White, M. A., Mei, F. C., Liu, T., Wang, D., Woods, V. L., Jr., and Cheng, X. (2011) Mechanism of intracellular cAMP sensor Epac2 activation: cAMP-induced conformational changes identified by amide hydrogen/deuterium exchange mass spectrometry (DXMS). J. Biol. Chem. 286, 17889-17897

30. Zhang, Z., and Smith, D. L. (1993) Determination of amide hydrogen exchange by mass spectrometry: a new tool for protein structure elucidation. Prot Science 2, 522-531

31. de Vries, S. J., van Dijk, M., and Bonvin, A. M. (2010) The HADDOCK web server for data-driven biomolecular docking. Nat. Prot. 5, 883-897

32. Marcatili, P., Olimpieri, P. P., Chailyan, A., and Tramontano, A. (2014) Antibody structural modeling with prediction of immunoglobulin structure (PIGS). Nat. Prot. 9, 2771-2783

33. Persson, H., Ye, W., Wemimont, A., Adams, J. J., Koide, A., Koide, S., Lam, R., and Sidhu, S. S. (2013) CDR-H3 diversity is not required for antigen recognition by synthetic antibodies. J. Mol. Biol. 425, 803-811

34. Yethon, J. A., Epand, R. F., Leber, B., Epand, R. M., and Andrews, D. W. (2003) Interaction with a membrane surface triggers a reversible conformational change in Bax normally associated with induction of apoptosis. J. Biol. Chem. 278, 48935-48941

35. Edwards, A. L., Gavathiotis, E., LaBelle, J. L., Braun, C. R, Opoku-Nsiah, K. A., Bird, G. H., and Walensky, L. D. (2013) Multimodal interaction with BCL-2 family proteins underlies the proapoptotic activity of PUMA BH3. Chem. & Biol. 20. 888-902

36. Leshchiner, E. S., Braun, C. R, Bird, G. H., and Walensky, L. D. (2013) Direct activation of full-length proapoptotic BAK. Proc. Nat. Acad. Sci. USA 110, E986-995

37. Ding, J., Mooers, B. H., Zhang, Z., Kale, J., Falcone, D., McNichol, J., Huang, B., Zhang, X. C., Xing, C., Andrews, D. W., and Lin, J. (2014) After embedding in membranes antiapoptotic Bcl-XL protein binds both Bcl-2 homology region 3 and helix 1 of proapoptotic Bax protein to inhibit apoptotic mitochondrial permeabilization. J. Biol. Chem. 289, 11873-11896

38. Ma, J., Edlich, F., Bermejo, G. A., Norris, K. L., Youle, R. J., and Tjandra, N. (2012) Structural mechanism of Bax inhibition by cytomegalovirus protein vMIA. Proc. Nat. Acad. Sci. USA 109, 20901-20906

39. Dominguez, C., Boelens, R., and Bonvin, A. M. (2003) HADDOCK: a protein-protein docking approach based on biochemical or biophysical information. J. Amer. Chem. Soc. 125, 1731-1737

40. Annis, M. G., Soucie, E. L., Dlugosz, P. J., Cruz-Aguado, J. A., Penn, L. Z., Leber, B., and Andrews, D. W. (2005) Bax forms multispanning monomers that oligomerize to permeabilize membranes during apoptosis. EMBO J. 24, 2096-2103

41. Tsai, C. J., Liu, S., Hung, C. L., Jhong, S. R, Sung, T. C., and Chiang, Y. W. (2015) BAX-induced apoptosis can be initiated through a conformational selection mechanism. Structure 23, 139-148

42. Gavathiotis, E., Reyna, D. E., Bellairs, J. A., Leshchiner, E. S., and Walensky, L. D. (2012) Direct and selective small-molecule activation of proapoptotic BAX. Nat. Chem. Biol. 8, 639-645

43. Billard, C. (2012) Development of Noxa-like BH3 mimetics for apoptosis-based therapeutic strategy in chronic lymphocytic leukemia. Mol. Cancer Res. 10, 673-676

What is claimed is:

1. A synthetic fragment antigen-binding (Fab) antibody that binds to an N-terminal activation site of BCL-2-associated X-protein (BAX) and inhibits BAX activation, wherein the synthetic fragment antigen-binding (Fab) antibody is selected from the group consisting of:

3H4 Fab, having a light chain comprising a CDR L1, a CDRL2, and a CDRL3 region comprising the amino acid sequence of SEQ.ID.No:69, wherein the CDRL3 region comprises QSWYYSYPI (SEQ ID NO: 25), and a heavy chain CDRH1 region comprising the amino acid sequence LSYSSM (SEQ ID NO: 26), a CDRH2 region comprising the amino acid sequence SISSYYSYTS (SEQ ID NO: 27), and a CDRH3 region comprising the amino acid sequence RYYGYGGGID (SEQ ID NO: 28);

2A6 Fab, having a light chain comprising a CDR L1, a CDRL2, and a CDRL3 region comprising the amino acid sequence of SEQ.ID.NO:75, wherein the CDRL3 region comprises QSAGGYPLI (SEQ ID NO: 29), and a heavy chain CDRH1 region comprising the amino acid sequence IYYSSM (SEQ ID NO: 30), a CDRH2 region comprising the amino acid sequence SISPYSSYTS (SEQ ID NO: 31), and a CDRH3 region comprising the amino acid sequence RSFGYGWAFD (SEQ ID NO: 32);

3H1 Fab, having a light chain comprising a CDR L1, a CDRL2, and a CDRL3 region comprising the amino acid sequence of SEQ.ID.NO:67, wherein the CDRL3 region comprises QHSYPI (SEQ ID NO: 33), and a heavy chain CDRHI region comprising the amino acid sequence ISYSSI (SEQ ID NO: 34), a CDRH2 region comprising the amino acid sequence SIYSYSGSTY (SEQ ID NO: 35), and a CDRH3 region comprising the amino acid sequence RYGAMD (SEQ ID NO: 36).

2. The synthetic Fab antibody of claim 1, wherein the antibody maintains BAX in its inactive, monomeric form.

3. The synthetic Fab antibody of claim 1, wherein the antibody binds to residues of helices α1 and α6, and to residues of α1-α2 loop of BAX.

4. The synthetic Fab antibody of claim 1, wherein the antibody binds to BAX with a half-maximal binding ($EC_{50}$) affinity of 2 nM-70 nM.

5. The synthetic Fab antibody of claim 1, wherein the antibody blocks the interaction of BAX with a BAX activating partner.

6. The synthetic Fab antibody of claim 5, wherein the BAX activating partner is selected from the group consisting of tBID, PUMA, BIM and NOXA.

7. The synthetic Fab antibody of claim 1, wherein the synthetic Fab antibody is conjugated to a therapeutic agent.

8. The synthetic Fab antibody of claim 1, wherein the synthetic Fab antibody is conjugated to an agent that facilitates transport across a cell membrane.

9. The synthetic Fab antibody of claim 1, wherein the synthetic Fab antibody is labeled with a fluorescent label or a radioactive label.

* * * * *

SEQUENCE LISTING

<160> NUMBER OF SEQ ID NOS: 90

<210> SEQ ID NO 1
<211> LENGTH: 10

```
<212> TYPE: PRT
<213> ORGANISM: Artificial Sequence
<220> FEATURE:
<223> OTHER INFORMATION: CDRL3 for Fab 2B1

<400> SEQUENCE: 1

Gln Tyr Ser Gly Ser Gly His Tyr Leu Ile
1               5                   10

<210> SEQ ID NO 2
<211> LENGTH: 6
<212> TYPE: PRT
<213> ORGANISM: Artificial Sequence
<220> FEATURE:
<223> OTHER INFORMATION: CDRH1 for Fab 2B1

<400> SEQUENCE: 2

Ile Tyr Ser Ser Ser Met
1               5

<210> SEQ ID NO 3
<211> LENGTH: 10
<212> TYPE: PRT
<213> ORGANISM: Artificial Sequence
<220> FEATURE:
<223> OTHER INFORMATION: CDRH2 for Fab 2B1

<400> SEQUENCE: 3

Ser Ile Ser Ser Ser Ser Ser Tyr Thr Ser
1               5                   10

<210> SEQ ID NO 4
<211> LENGTH: 15
<212> TYPE: PRT
<213> ORGANISM: Artificial Sequence
<220> FEATURE:
<223> OTHER INFORMATION: CDRH3 for Fab 2B1

<400> SEQUENCE: 4

Arg Gly Tyr Trp Tyr Tyr Trp Ala Trp Trp Ala Ser Ala Met Asp
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: CDRL3 for Fab 3E8

<400> SEQUENCE: 5

Gln Ser Ser Tyr Ser Leu Ile
1               5

<210> SEQ ID NO 6
<211> LENGTH: 6
<212> TYPE: PRT
<213> ORGANISM: Artificial Sequence
<220> FEATURE:
<223> OTHER INFORMATION: CDRH1 for Fab 3E8

<400> SEQUENCE: 6

Leu Ser Tyr Tyr Ser Met
1               5

<210> SEQ ID NO 7
<211> LENGTH: 10
<212> TYPE: PRT
```

<213> ORGANISM: Artificial Sequence
<220> FEATURE:
<223> OTHER INFORMATION: CDRH2 for Fab 3E8

<400> SEQUENCE: 7

Ser Ile Ser Pro Tyr Tyr Gly Tyr Thr Tyr
1               5                   10

<210> SEQ ID NO 8
<211> LENGTH: 18
<212> TYPE: PRT
<213> ORGANISM: Artificial Sequence
<220> FEATURE:
<223> OTHER INFORMATION: CDRH3 for Fab 3E8

<400> SEQUENCE: 8

Arg Gly Gly Ala Tyr Tyr Phe Gly Tyr Tyr Gly Ser Gly Ser Tyr Ala
1               5                   10                  15

Met Asp

<210> SEQ ID NO 9
<211> LENGTH: 7
<212> TYPE: PRT
<213> ORGANISM: Artificial Sequence
<220> FEATURE:
<223> OTHER INFORMATION: CDRL3 for Fab 3G11

<400> SEQUENCE: 9

Gln Trp Ser Phe Gly Pro Ile
1               5

<210> SEQ ID NO 10
<211> LENGTH: 6
<212> TYPE: PRT
<213> ORGANISM: Artificial Sequence
<220> FEATURE:
<223> OTHER INFORMATION: CDRH1 for Fab 3G11

<400> SEQUENCE: 10

Ile Ser Tyr Tyr Ser Met
1               5

<210> SEQ ID NO 11
<211> LENGTH: 10
<212> TYPE: PRT
<213> ORGANISM: Artificial Sequence
<220> FEATURE:
<223> OTHER INFORMATION: CDRH2 for Fab 3G11

<400> SEQUENCE: 11

Ser Ile Tyr Pro Tyr Ser Ser Ser Thr Tyr
1               5                   10

<210> SEQ ID NO 12
<211> LENGTH: 6
<212> TYPE: PRT
<213> ORGANISM: Artificial Sequence
<220> FEATURE:
<223> OTHER INFORMATION: CDRH3 for Fab 3G11

<400> SEQUENCE: 12

Arg Ser Ser Ala Met Asp
1               5

<210> SEQ ID NO 13
<211> LENGTH: 7

```
<212> TYPE: PRT
<213> ORGANISM: Artificial Sequence
<220> FEATURE:
<223> OTHER INFORMATION: CDRL3 for Fab 2D9

<400> SEQUENCE: 13

Gln Trp Ser His Tyr Leu Ile
1               5

<210> SEQ ID NO 14
<211> LENGTH: 6
<212> TYPE: PRT
<213> ORGANISM: Artificial Sequence
<220> FEATURE:
<223> OTHER INFORMATION: CDRH1 for Fab 2D9

<400> SEQUENCE: 14

Leu Tyr Tyr Tyr Ser Met
1               5

<210> SEQ ID NO 15
<211> LENGTH: 10
<212> TYPE: PRT
<213> ORGANISM: Artificial Sequence
<220> FEATURE:
<223> OTHER INFORMATION: CDRH2 for Fab 2D9

<400> SEQUENCE: 15

Ser Ile Ser Pro Ser Tyr Gly Tyr Thr Ser
1               5                   10

<210> SEQ ID NO 16
<211> LENGTH: 10
<212> TYPE: PRT
<213> ORGANISM: Artificial Sequence
<220> FEATURE:
<223> OTHER INFORMATION: CDRH3 for Fab 2D9

<400> SEQUENCE: 16

Arg Ser Ser Phe Tyr Tyr Tyr Ala Leu Asp
1               5                   10

<210> SEQ ID NO 17
<211> LENGTH: 10
<212> TYPE: PRT
<213> ORGANISM: Artificial Sequence
<220> FEATURE:
<223> OTHER INFORMATION: CDRL3 for Fab 3G9

<400> SEQUENCE: 17

Gln His Tyr Tyr Tyr Ser Pro Trp Pro Ile
1               5                   10

<210> SEQ ID NO 18
<211> LENGTH: 6
<212> TYPE: PRT
<213> ORGANISM: Artificial Sequence
<220> FEATURE:
<223> OTHER INFORMATION: CDRH1 for Fab 3G9

<400> SEQUENCE: 18

Leu Tyr Ser Tyr Tyr Ile
1               5

<210> SEQ ID NO 19
<211> LENGTH: 10
<212> TYPE: PRT
```

```
<213> ORGANISM: Artificial Sequence
<220> FEATURE:
<223> OTHER INFORMATION: CDRH2 for Fab 3G9

<400> SEQUENCE: 19

Ser Ile Ser Pro Tyr Tyr Ser Ser Thr Tyr
1               5                   10

<210> SEQ ID NO 20
<211> LENGTH: 10
<212> TYPE: PRT
<213> ORGANISM: Artificial Sequence
<220> FEATURE:
<223> OTHER INFORMATION: CDRH3 for Fab 3G9

<400> SEQUENCE: 20

Arg Ser Ser Tyr Ser Tyr Ala Gly Met Asp
1               5                   10

<210> SEQ ID NO 21
<211> LENGTH: 7
<212> TYPE: PRT
<213> ORGANISM: Artificial Sequence
<220> FEATURE:
<223> OTHER INFORMATION: CDRL3 for Fab 2C11

<400> SEQUENCE: 21

Gln Ser Tyr Val Ser Pro Ile
1               5

<210> SEQ ID NO 22
<211> LENGTH: 6
<212> TYPE: PRT
<213> ORGANISM: Artificial Sequence
<220> FEATURE:
<223> OTHER INFORMATION: CDRH1 for Fab 2C11

<400> SEQUENCE: 22

Ile Ser Ser Tyr Tyr Ile
1               5

<210> SEQ ID NO 23
<211> LENGTH: 10
<212> TYPE: PRT
<213> ORGANISM: Artificial Sequence
<220> FEATURE:
<223> OTHER INFORMATION: CDRH2 for Fab 2C11

<400> SEQUENCE: 23

Ser Ile Ser Ser Tyr Tyr Ser Ser Thr Tyr
1               5                   10

<210> SEQ ID NO 24
<211> LENGTH: 16
<212> TYPE: PRT
<213> ORGANISM: Artificial Sequence
<220> FEATURE:
<223> OTHER INFORMATION: CDRH3 for Fab 2C11

<400> SEQUENCE: 24

Arg Val Ser Tyr Gly His Ala Tyr Val Gly Tyr Ser Ser Gly Met Asp
1               5                   10                  15

<210> SEQ ID NO 25
<211> LENGTH: 9
<212> TYPE: PRT
<213> ORGANISM: Artificial Sequence
```

<220> FEATURE:
<223> OTHER INFORMATION: CDRL3 for Fab 3H4

<400> SEQUENCE: 25

Gln Ser Trp Tyr Tyr Ser Tyr Pro Ile
1               5

<210> SEQ ID NO 26
<211> LENGTH: 6
<212> TYPE: PRT
<213> ORGANISM: Artificial Sequence
<220> FEATURE:
<223> OTHER INFORMATION: CDRH1 for Fab 3H4

<400> SEQUENCE: 26

Leu Ser Tyr Ser Ser Met
1               5

<210> SEQ ID NO 27
<211> LENGTH: 10
<212> TYPE: PRT
<213> ORGANISM: Artificial Sequence
<220> FEATURE:
<223> OTHER INFORMATION: CDRH2 for Fab 3H4

<400> SEQUENCE: 27

Ser Ile Ser Ser Tyr Tyr Ser Tyr Thr Ser
1               5                   10

<210> SEQ ID NO 28
<211> LENGTH: 10
<212> TYPE: PRT
<213> ORGANISM: Artificial Sequence
<220> FEATURE:
<223> OTHER INFORMATION: CDRH3 for Fab 3H4

<400> SEQUENCE: 28

Arg Tyr Tyr Gly Tyr Gly Gly Gly Ile Asp
1               5                   10

<210> SEQ ID NO 29
<211> LENGTH: 9
<212> TYPE: PRT
<213> ORGANISM: Artificial Sequence
<220> FEATURE:
<223> OTHER INFORMATION: CDRL3 for Fab 2A6

<400> SEQUENCE: 29

Gln Ser Ala Gly Gly Tyr Pro Leu Ile
1               5

<210> SEQ ID NO 30
<211> LENGTH: 6
<212> TYPE: PRT
<213> ORGANISM: Artificial Sequence
<220> FEATURE:
<223> OTHER INFORMATION: CDRH1 for Fab 2A6

<400> SEQUENCE: 30

Ile Tyr Tyr Ser Ser Met
1               5

<210> SEQ ID NO 31
<211> LENGTH: 10
<212> TYPE: PRT
<213> ORGANISM: Artificial Sequence
<220> FEATURE:

<223> OTHER INFORMATION: CDRH2 for Fab 2A6

<400> SEQUENCE: 31

Ser Ile Ser Pro Tyr Ser Ser Tyr Thr Ser
1               5                   10

<210> SEQ ID NO 32
<211> LENGTH: 10
<212> TYPE: PRT
<213> ORGANISM: Artificial Sequence
<220> FEATURE:
<223> OTHER INFORMATION: CDRH3 for Fab 2A6

<400> SEQUENCE: 32

Arg Ser Phe Gly Tyr Gly Trp Ala Phe Asp
1               5                   10

<210> SEQ ID NO 33
<211> LENGTH: 6
<212> TYPE: PRT
<213> ORGANISM: Artificial Sequence
<220> FEATURE:
<223> OTHER INFORMATION: CDRL3 for Fab 3H1

<400> SEQUENCE: 33

Gln His Ser Tyr Pro Ile
1               5

<210> SEQ ID NO 34
<211> LENGTH: 6
<212> TYPE: PRT
<213> ORGANISM: Artificial Sequence
<220> FEATURE:
<223> OTHER INFORMATION: CDRH1 for Fab 3H1

<400> SEQUENCE: 34

Ile Ser Tyr Ser Ser Ile
1               5

<210> SEQ ID NO 35
<211> LENGTH: 10
<212> TYPE: PRT
<213> ORGANISM: Artificial Sequence
<220> FEATURE:
<223> OTHER INFORMATION: CDRH2 for Fab 3H1

<400> SEQUENCE: 35

Ser Ile Tyr Ser Tyr Ser Gly Ser Thr Tyr
1               5                   10

<210> SEQ ID NO 36
<211> LENGTH: 6
<212> TYPE: PRT
<213> ORGANISM: Artificial Sequence
<220> FEATURE:
<223> OTHER INFORMATION: CDRH3 for Fab 3H1

<400> SEQUENCE: 36

Arg Tyr Gly Ala Met Asp
1               5

<210> SEQ ID NO 37
<211> LENGTH: 6
<212> TYPE: PRT
<213> ORGANISM: Artificial Sequence
<220> FEATURE:
<223> OTHER INFORMATION: CDRL3 for Fab 2A2

```
<400> SEQUENCE: 37

Gln Tyr Tyr Tyr Pro Ile
1               5

<210> SEQ ID NO 38
<211> LENGTH: 6
<212> TYPE: PRT
<213> ORGANISM: Artificial Sequence
<220> FEATURE:
<223> OTHER INFORMATION: CDRH1 for Fab 2A2

<400> SEQUENCE: 38

Ile Ser Ser Ser Ser Ile
1               5

<210> SEQ ID NO 39
<211> LENGTH: 10
<212> TYPE: PRT
<213> ORGANISM: Artificial Sequence
<220> FEATURE:
<223> OTHER INFORMATION: CDRH2 for Fab 2A2

<400> SEQUENCE: 39

Ser Ile Tyr Ser Tyr Tyr Gly Tyr Thr Tyr
1               5                   10

<210> SEQ ID NO 40
<211> LENGTH: 6
<212> TYPE: PRT
<213> ORGANISM: Artificial Sequence
<220> FEATURE:
<223> OTHER INFORMATION: CDRH3 for Fab 2A2

<400> SEQUENCE: 40

Arg Tyr Ser Ala Met Asp
1               5

<210> SEQ ID NO 41
<211> LENGTH: 10
<212> TYPE: PRT
<213> ORGANISM: Artificial Sequence
<220> FEATURE:
<223> OTHER INFORMATION: CDRL3 for Fab 3G3

<400> SEQUENCE: 41

Gln Gly Ala Trp Ser Gly Gly His Leu Ile
1               5                   10

<210> SEQ ID NO 42
<211> LENGTH: 6
<212> TYPE: PRT
<213> ORGANISM: Artificial Sequence
<220> FEATURE:
<223> OTHER INFORMATION: CDRH1 for Fab 3G3

<400> SEQUENCE: 42

Leu Ser Tyr Ser Ser Met
1               5

<210> SEQ ID NO 43
<211> LENGTH: 10
<212> TYPE: PRT
<213> ORGANISM: Artificial Sequence
<220> FEATURE:
<223> OTHER INFORMATION: CDRH2 for Fab 3G3
```

```
<400> SEQUENCE: 43

Tyr Ile Ser Pro Tyr Tyr Gly Tyr Thr Tyr
1               5                   10

<210> SEQ ID NO 44
<211> LENGTH: 16
<212> TYPE: PRT
<213> ORGANISM: Artificial Sequence
<220> FEATURE:
<223> OTHER INFORMATION: CDRH3 for Fab 3G3

<400> SEQUENCE: 44

Arg Gly Trp Ala Tyr Tyr Tyr Gly Tyr Trp Gly Pro Ser Gly Leu Asp
1               5                   10                  15

<210> SEQ ID NO 45
<211> LENGTH: 10
<212> TYPE: PRT
<213> ORGANISM: Artificial Sequence
<220> FEATURE:
<223> OTHER INFORMATION: CDRL3 for Fab 2D5

<400> SEQUENCE: 45

Gln Trp Gly Tyr Ser His Ser His Leu Ile
1               5                   10

<210> SEQ ID NO 46
<211> LENGTH: 5
<212> TYPE: PRT
<213> ORGANISM: Artificial Sequence
<220> FEATURE:
<223> OTHER INFORMATION: CDRH1 for Fab 2D5

<400> SEQUENCE: 46

Ile Ser Tyr Ser Ser
1               5

<210> SEQ ID NO 47
<211> LENGTH: 10
<212> TYPE: PRT
<213> ORGANISM: Artificial Sequence
<220> FEATURE:
<223> OTHER INFORMATION: CDRH2 for Fab 2D5

<400> SEQUENCE: 47

Ser Ile Ser Pro Tyr Tyr Gly Ser Thr Tyr
1               5                   10

<210> SEQ ID NO 48
<211> LENGTH: 8
<212> TYPE: PRT
<213> ORGANISM: Artificial Sequence
<220> FEATURE:
<223> OTHER INFORMATION: CDRH3 for Fab 2D5

<400> SEQUENCE: 48

Arg Ser His Phe Gly Ala Leu Asp
1               5

<210> SEQ ID NO 49
<211> LENGTH: 9
<212> TYPE: PRT
<213> ORGANISM: Artificial Sequence
<220> FEATURE:
<223> OTHER INFORMATION: CDRL3 for Fab 2D2

<400> SEQUENCE: 49
```

```
Gln Ser Tyr Tyr Trp Val Ser Pro Phe
1               5

<210> SEQ ID NO 50
<211> LENGTH: 6
<212> TYPE: PRT
<213> ORGANISM: Artificial Sequence
<220> FEATURE:
<223> OTHER INFORMATION: CDRH1 for Fab 2D2

<400> SEQUENCE: 50

Leu Tyr Tyr Ser Ser Ile
1               5

<210> SEQ ID NO 51
<211> LENGTH: 10
<212> TYPE: PRT
<213> ORGANISM: Artificial Sequence
<220> FEATURE:
<223> OTHER INFORMATION: CDRH2 for Fab 2D2

<400> SEQUENCE: 51

Ser Ile Tyr Pro Tyr Ser Gly Ser Thr Tyr
1               5                   10

<210> SEQ ID NO 52
<211> LENGTH: 8
<212> TYPE: PRT
<213> ORGANISM: Artificial Sequence
<220> FEATURE:
<223> OTHER INFORMATION: CDRH3 for Fab 2D2

<400> SEQUENCE: 52

Arg Ser Tyr Gly Tyr Ala Met Asp
1               5

<210> SEQ ID NO 53
<211> LENGTH: 9
<212> TYPE: PRT
<213> ORGANISM: Artificial Sequence
<220> FEATURE:
<223> OTHER INFORMATION: CDRL3 for Fab 2A5

<400> SEQUENCE: 53

Gln Tyr His Tyr Trp Tyr Tyr Pro Ile
1               5

<210> SEQ ID NO 54
<211> LENGTH: 6
<212> TYPE: PRT
<213> ORGANISM: Artificial Sequence
<220> FEATURE:
<223> OTHER INFORMATION: CDRH1 for Fab 2A5

<400> SEQUENCE: 54

Ile Ser Tyr Tyr Ser Met
1               5

<210> SEQ ID NO 55
<211> LENGTH: 10
<212> TYPE: PRT
<213> ORGANISM: Artificial Sequence
<220> FEATURE:
<223> OTHER INFORMATION: CDRH2 for Fab 2A5

<400> SEQUENCE: 55
```

```
Ser Ile Ser Pro Tyr Tyr Gly Ser Thr Tyr
1               5                   10
```

<210> SEQ ID NO 56
<211> LENGTH: 6
<212> TYPE: PRT
<213> ORGANISM: Artificial Sequence
<220> FEATURE:
<223> OTHER INFORMATION: CDRH3 for Fab 2A5

<400> SEQUENCE: 56

```
Arg Ala Gly Ala Met Asp
1               5
```

<210> SEQ ID NO 57
<211> LENGTH: 192
<212> TYPE: PRT
<213> ORGANISM: Homo sapiens

<400> SEQUENCE: 57

```
Met Asp Gly Ser Gly Glu Gln Pro Arg Gly Gly Gly Pro Thr Ser Ser
1               5                   10                  15

Glu Gln Ile Met Lys Thr Gly Ala Leu Leu Leu Gln Gly Phe Ile Gln
                20                  25                  30

Asp Arg Ala Gly Arg Met Gly Gly Glu Ala Pro Glu Leu Ala Leu Asp
            35                  40                  45

Pro Val Pro Gln Asp Ala Ser Thr Lys Lys Leu Ser Glu Cys Leu Lys
        50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                85                  90                  95

Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190
```

<210> SEQ ID NO 58
<211> LENGTH: 242
<212> TYPE: PRT
<213> ORGANISM: Artificial Sequence
<220> FEATURE:
<223> OTHER INFORMATION: heavy chain of Fab 3E8

<400> SEQUENCE: 58

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Ser Tyr Tyr
                20                  25                  30

Ser Met His Trp Val Arg Gln Ala Pro Gly Lys Gly Leu Glu Trp Val
            35                  40                  45
```

```
Ala Ser Ile Ser Pro Tyr Tyr Gly Tyr Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Gly Ala Tyr Tyr Phe Gly Tyr Gly Ser Gly Ser Tyr
             100                 105                 110

Ala Met Asp Tyr Trp Gly Gln Gly Thr Leu Val Thr Val Ser Ser Ala
             115                 120                 125

Ser Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                 165                 170                 175

Val His Thr Phe Pro Ala Val Leu Gln Ser Ser Gly Leu Tyr Ser Leu
             180                 185                 190

Ser Ser Val Val Thr Val Pro Ser Ser Ser Leu Gly Thr Gln Thr Tyr
         195                 200                 205

Ile Cys Asn Val Asn His Lys Pro Ser Asn Thr Lys Val Asp Lys Lys
210                 215                 220

Val Glu Pro Lys Ser Cys Asp Lys Thr His Thr Cys His His His His
225                 230                 235                 240

His His

<210> SEQ ID NO 59
<211> LENGTH: 225
<212> TYPE: PRT
<213> ORGANISM: Artificial Sequence
<220> FEATURE:
<223> OTHER INFORMATION: light chain of Fab 3E8

<400> SEQUENCE: 59

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
             20                  25                  30

Val Ala Trp Tyr Gln Gln Lys Pro Gly Lys Ala Pro Lys Leu Leu Ile
         35                  40                  45

Tyr Ser Ala Ser Ser Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Ser Tyr Ser Leu Ile
                 85                  90                  95

Thr Phe Gly Gln Gly Thr Lys Val Glu Ile Lys Arg Thr Val Ala Ala
             100                 105                 110

Pro Ser Val Phe Ile Phe Pro Pro Ser Asp Ser Gln Leu Lys Ser Gly
             115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                    165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Ser Asp Tyr Lys Asp Asp Asp
    210                 215                 220

Lys
225

<210> SEQ ID NO 60
<211> LENGTH: 240
<212> TYPE: PRT
<213> ORGANISM: Artificial Sequence
<220> FEATURE:
<223> OTHER INFORMATION: heavy chain of Fab 3G3

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Ser Tyr Ser
            20                  25                  30

Ser Met His Trp Val Arg Gln Ala Pro Gly Lys Gly Leu Glu Trp Val
        35                  40                  45

Ala Tyr Ile Ser Pro Tyr Tyr Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Trp Ala Tyr Tyr Gly Tyr Trp Gly Pro Ser Gly Leu
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys His His His His His
225                 230                 235                 240

<210> SEQ ID NO 61
<211> LENGTH: 228
<212> TYPE: PRT
<213> ORGANISM: Artificial Sequence
<220> FEATURE:
<223> OTHER INFORMATION: light chain of Fab 3G3
<220> FEATURE:
<221> NAME/KEY: MISC_FEATURE
<222> LOCATION: (202)..(202)
```

<223> OTHER INFORMATION: Xaa can be any naturally occurring amino acid

<400> SEQUENCE: 61

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Val Ser Ser Ala
            20                  25                  30
Val Ala Trp Tyr Gln Gln Lys Pro Gly Lys Ala Pro Lys Leu Leu Ile
        35                  40                  45
Tyr Ser Ala Ser Ser Leu Tyr Ser Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln Gly Ala Trp Ser Gly Gly
                85                  90                  95
His Leu Ile Thr Phe Gly Gln Gly Thr Lys Val Glu Ile Lys Arg Thr
            100                 105                 110
Val Ala Ala Pro Ser Val Phe Ile Phe Pro Pro Ser Asp Ser Gln Leu
        115                 120                 125
Lys Ser Gly Thr Ala Ser Val Val Cys Leu Leu Asn Asn Phe Tyr Pro
    130                 135                 140
Arg Glu Ala Lys Val Gln Trp Lys Val Asp Asn Ala Leu Gln Ser Gly
145                 150                 155                 160
Asn Ser Gln Glu Ser Val Thr Glu Gln Asp Ser Lys Asp Ser Thr Tyr
                165                 170                 175
Ser Leu Ser Ser Thr Leu Thr Leu Ser Lys Ala Asp Tyr Glu Lys His
            180                 185                 190
Lys Val Tyr Ala Cys Glu Val Thr His Xaa Gly Leu Ser Ser Pro Val
        195                 200                 205
Thr Lys Ser Phe Asn Arg Gly Glu Cys Gly Gly Ser Asp Tyr Lys Asp
    210                 215                 220
Asp Asp Asp Lys
225
```

<210> SEQ ID NO 62
<211> LENGTH: 234
<212> TYPE: PRT
<213> ORGANISM: Artificial Sequence
<220> FEATURE:
<223> OTHER INFORMATION: heavy chain of Fab 3G9

<400> SEQUENCE: 62

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Leu Tyr Ser Tyr
            20                  25                  30
Tyr Ile His Trp Val Arg Gln Ala Pro Gly Lys Gly Leu Glu Trp Val
        35                  40                  45
Ala Ser Ile Ser Pro Tyr Tyr Ser Ser Thr Tyr Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Ser Ser Tyr Ser Tyr Ala Gly Met Asp Tyr Trp Gly Gln Gly
            100                 105                 110
```

```
Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys His His His His His His
225                 230

<210> SEQ ID NO 63
<211> LENGTH: 228
<212> TYPE: PRT
<213> ORGANISM: Artificial Sequence
<220> FEATURE:
<223> OTHER INFORMATION: light chain of Fab 3G9

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Tyr Tyr Ser Pro
                85                  90                  95

Trp Pro Ile Thr Phe Gly Gln Gly Thr Lys Val Glu Ile Lys Arg Thr
            100                 105                 110

Val Ala Ala Pro Ser Val Phe Ile Phe Pro Pro Ser Asp Ser Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys Gly Gly Ser Asp Tyr Lys Asp
    210                 215                 220

Asp Asp Asp Lys
225
```

<210> SEQ ID NO 64
<211> LENGTH: 230
<212> TYPE: PRT
<213> ORGANISM: Artificial Sequence
<220> FEATURE:
<223> OTHER INFORMATION: heavy chain of Fab 3G11

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Tyr
            20                  25                  30

Ser Met His Trp Val Arg Gln Ala Pro Gly Lys Gly Leu Glu Trp Val
        35                  40                  45

Ala Ser Ile Tyr Pro Tyr Ser Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Ala Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

His His His His His His
225                 230

<210> SEQ ID NO 65
<211> LENGTH: 225
<212> TYPE: PRT
<213> ORGANISM: Artificial Sequence
<220> FEATURE:
<223> OTHER INFORMATION: light chain of Fab 3G11

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro

-continued

```
                65                  70                  75                  80
Glu Asp Phe Ala Thr Tyr Tyr Cys Gln Gln Trp Ser Phe Gly Pro Ile
                    85                  90                  95
Thr Phe Gly Gln Gly Thr Lys Val Glu Ile Lys Arg Thr Val Ala Ala
                100                 105                 110
Pro Ser Val Phe Ile Phe Pro Pro Ser Asp Ser Gln Leu Lys Ser Gly
                115                 120                 125
Thr Ala Ser Val Val Cys Leu Leu Asn Asn Phe Tyr Pro Arg Glu Ala
            130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
                180                 185                 190
Ala Cys Glu Val Thr His Gln Gly Leu Ser Ser Pro Val Thr Lys Ser
                195                 200                 205
Phe Asn Arg Gly Glu Cys Gly Gly Ser Asp Tyr Lys Asp Asp Asp Asp
            210                 215                 220
Lys
225
```

```
<210> SEQ ID NO 66
<211> LENGTH: 230
<212> TYPE: PRT
<213> ORGANISM: Artificial Sequence
<220> FEATURE:
<223> OTHER INFORMATION: heavy chain of Fab 3H1

<400> SEQUENCE: 66

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Ser Tyr Ser
                20                  25                  30
Ser Ile His Trp Val Arg Gln Ala Pro Gly Lys Gly Leu Glu Trp Val
            35                  40                  45
Ala Ser Ile Tyr Ser Tyr Ser Gly Ser Thr Tyr Tyr Ala Asp Ser Val
        50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Tyr Gly Ala Met Asp Tyr Trp Gly Gln Gly Thr Leu Val Thr
                100                 105                 110
Val Ser Ser Ala Ser Thr Lys Gly Pro Ser Val Phe Pro Leu Ala Pro
            115                 120                 125
Ser Ser Lys Ser Thr Ser Gly Gly Thr Ala Ala Leu Gly Cys Leu Val
        130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
                180                 185                 190
Thr Gln Thr Tyr Ile Cys Asn Val Asn His Lys Pro Ser Asn Thr Lys
```

```
             195                 200                 205
Val Asp Lys Lys Val Glu Pro Lys Ser Cys Asp Lys Thr His Thr Cys
210                 215                 220

His His His His His His
225                 230

<210> SEQ ID NO 67
<211> LENGTH: 224
<212> TYPE: PRT
<213> ORGANISM: Artificial Sequence
<220> FEATURE:
<223> OTHER INFORMATION: light chain of Fab 3H1

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Ser Tyr Pro Ile Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Ser Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Gly Gly Ser Asp Tyr Lys Asp Asp Asp Lys
210                 215                 220

<210> SEQ ID NO 68
<211> LENGTH: 234
<212> TYPE: PRT
<213> ORGANISM: Artificial Sequence
<220> FEATURE:
<223> OTHER INFORMATION: heavy chain of Fab 3H4

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Ser Tyr Ser
            20                  25                  30

Ser Met His Trp Val Arg Gln Ala Pro Gly Lys Gly Leu Glu Trp Val
        35                  40                  45
```

```
Ala Ser Ile Ser Ser Tyr Tyr Ser Tyr Thr Ser Tyr Ala Asp Ser Val
    50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Tyr Tyr Gly Tyr Gly Gly Ile Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys His His His His His His
225                 230

<210> SEQ ID NO 69
<211> LENGTH: 227
<212> TYPE: PRT
<213> ORGANISM: Artificial Sequence
<220> FEATURE:
<223> OTHER INFORMATION: light chain of Fab 3H4

<400> SEQUENCE: 69

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
             20                  25                  30

Val Ala Trp Tyr Gln Gln Lys Pro Gly Lys Ala Pro Lys Leu Leu Ile
         35                  40                  45

Tyr Ser Ala Ser Ser Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Trp Tyr Tyr Ser Tyr
                 85                  90                  95

Pro Ile Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175
```

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Gly Gly Ser Asp Tyr Lys Asp Asp
    210                 215                 220

Asp Asp Lys
225

<210> SEQ ID NO 70
<211> LENGTH: 230
<212> TYPE: PRT
<213> ORGANISM: Artificial Sequence
<220> FEATURE:
<223> OTHER INFORMATION: heavy chain of Fab 2A2

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Ser Ser
            20                  25                  30

Ser Ile His Trp Val Arg Gln Ala Pro Gly Lys Gly Leu Glu Trp Val
        35                  40                  45

Ala Ser Ile Tyr Ser Tyr Tyr Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Ser Ala Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

His His His His His His
225                 230

<210> SEQ ID NO 71
<211> LENGTH: 224
<212> TYPE: PRT
<213> ORGANISM: Artificial Sequence
<220> FEATURE:
<223> OTHER INFORMATION: light chain of Fab 2A2

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Pro Ile Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Ser Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Gly Gly Ser Asp Tyr Lys Asp Asp Asp Lys
    210                 215                 220

<210> SEQ ID NO 72
<211> LENGTH: 230
<212> TYPE: PRT
<213> ORGANISM: Artificial Sequence
<220> FEATURE:
<223> OTHER INFORMATION: heavy chain of Fab 2A5

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Ser Ser
            20                  25                  30

Ser Met His Trp Val Arg Gln Ala Pro Gly Lys Gly Leu Glu Trp Val
        35                  40                  45

Ala Ser Ile Ser Ser Ser Ser Tyr Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Gly Ala Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

```
Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

His His His His His His
225                 230

<210> SEQ ID NO 73
<211> LENGTH: 227
<212> TYPE: PRT
<213> ORGANISM: Artificial Sequence
<220> FEATURE:
<223> OTHER INFORMATION: light chain of Fab 2A5
<220> FEATURE:
<221> NAME/KEY: MISC_FEATURE
<222> LOCATION: (201)..(201)
<223> OTHER INFORMATION: Xaa can be any naturally occurring amino acid

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His Tyr Trp Tyr Tyr
                85                  90                  95

Pro Ile Thr Phe Gly Gln Gly Thr Lys Val Glu Ile Lys Arg Thr Val
            100                 105                 110

Ala Ala Pro Ser Val Phe Ile Phe Pro Pro Ser Asp Ser Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Xaa Gly Leu Ser Ser Pro Val Thr
        195                 200                 205

Lys Ser Phe Asn Arg Gly Glu Cys Gly Gly Ser Asp Tyr Lys Asp Asp
210                 215                 220

Asp Asp Lys
225

<210> SEQ ID NO 74
<211> LENGTH: 234
<212> TYPE: PRT
```

<213> ORGANISM: Artificial Sequence
<220> FEATURE:
<223> OTHER INFORMATION: heavy chain of Fab 2A6

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Tyr Ser
            20                  25                  30

Ser Met His Trp Val Arg Gln Ala Pro Gly Lys Gly Leu Glu Trp Val
        35                  40                  45

Ala Ser Ile Ser Pro Tyr Ser Ser Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Phe Gly Tyr Gly Trp Ala Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys His His His His His His
225                 230

<210> SEQ ID NO 75
<211> LENGTH: 227
<212> TYPE: PRT
<213> ORGANISM: Artificial Sequence
<220> FEATURE:
<223> OTHER INFORMATION: light chain of Fab 2A6
<220> FEATURE:
<221> NAME/KEY: MISC_FEATURE
<222> LOCATION: (201)..(201)
<223> OTHER INFORMATION: Xaa can be any naturally occurring amino acid

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

```
Glu Asp Phe Ala Thr Tyr Tyr Cys Gln Gln Ser Ala Gly Gly Tyr Pro
                85                  90                  95

Leu Ile Thr Phe Gly Gln Gly Thr Lys Val Glu Ile Lys Arg Thr Val
            100                 105                 110

Ala Ala Pro Ser Val Phe Ile Phe Pro Pro Ser Asp Ser Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Xaa Gly Leu Ser Ser Pro Val Thr
        195                 200                 205

Lys Ser Phe Asn Arg Gly Glu Cys Gly Gly Ser Asp Tyr Lys Asp Asp
    210                 215                 220

Asp Asp Lys
225

<210> SEQ ID NO 76
<211> LENGTH: 239
<212> TYPE: PRT
<213> ORGANISM: Artificial Sequence
<220> FEATURE:
<223> OTHER INFORMATION: heavy chain of Fab 2B1

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Ser Ser
            20                  25                  30

Ser Met His Trp Val Arg Gln Ala Pro Gly Lys Gly Leu Glu Trp Val
        35                  40                  45

Ala Ser Ile Ser Ser Ser Ser Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Trp Tyr Tyr Trp Ala Trp Trp Ala Ser Ala Met Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205
```

Val Asn His Lys Pro Ser Asn Thr Lys Val Asp Lys Val Glu Pro
         210                 215                 220

Lys Ser Cys Asp Lys Thr His Thr Cys His His His His His His
225                 230                 235

```
<210> SEQ ID NO 77
<211> LENGTH: 228
<212> TYPE: PRT
<213> ORGANISM: Artificial Sequence
<220> FEATURE:
<223> OTHER INFORMATION: light chain of Fab 2B1

<400> SEQUENCE: 77
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Gly Ser Gly His
                85                  90                  95

Tyr Leu Ile Thr Phe Gly Gln Gly Thr Lys Val Glu Ile Lys Arg Thr
            100                 105                 110

Val Ala Ala Pro Ser Val Phe Ile Phe Pro Pro Ser Asp Ser Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys Gly Gly Ser Asp Tyr Lys Asp
210                 215                 220

Asp Asp Asp Lys
225

```
<210> SEQ ID NO 78
<211> LENGTH: 240
<212> TYPE: PRT
<213> ORGANISM: Artificial Sequence
<220> FEATURE:
<223> OTHER INFORMATION: heavy chain of Fab 2C11

<400> SEQUENCE: 78
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Ser Tyr
            20                  25                  30

Tyr Ile His Trp Val Arg Gln Ala Pro Gly Lys Gly Leu Glu Trp Val

```
            35                  40                  45
Ala Ser Ile Ser Ser Tyr Tyr Ser Ser Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Val Ser Tyr Gly His Ala Tyr Val Gly Tyr Ser Ser Gly Met
                100                 105                 110

Asp Tyr Trp Gly Gln Gly Thr Leu Val Thr Val Ser Ser Ala Ser Thr
             115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys His His His His His His
225                 230                 235                 240

<210> SEQ ID NO 79
<211> LENGTH: 225
<212> TYPE: PRT
<213> ORGANISM: Artificial Sequence
<220> FEATURE:
<223> OTHER INFORMATION: light chain of Fab 2C11
<220> FEATURE:
<221> NAME/KEY: MISC_FEATURE
<222> LOCATION: (166)..(166)
<223> OTHER INFORMATION: Xaa can be any naturally occurring amino acid
<220> FEATURE:
<221> NAME/KEY: MISC_FEATURE
<222> LOCATION: (199)..(199)
<223> OTHER INFORMATION: Xaa can be any naturally occurring amino acid

<400> SEQUENCE: 79

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Val Ser Ser Ala
                 20                  25                  30

Val Ala Trp Tyr Gln Gln Lys Pro Gly Lys Ala Pro Lys Leu Leu Ile
             35                  40                  45

Tyr Ser Ala Ser Ser Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Val Ser Pro Ile
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Ser Gln Leu Lys Ser Gly
        115                 120                 125
```

```
Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Xaa Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Xaa Gly Leu Ser Ser Pro Val Thr Lys Ser
            195                 200                 205

Phe Asn Arg Gly Glu Cys Gly Ser Asp Tyr Lys Asp Asp Asp
210                 215                 220

Lys
225

<210> SEQ ID NO 80
<211> LENGTH: 232
<212> TYPE: PRT
<213> ORGANISM: Artificial Sequence
<220> FEATURE:
<223> OTHER INFORMATION: heavy chain of Fab 2D2

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
                20                  25                  30

Ser Ile His Trp Val Arg Gln Ala Pro Gly Lys Gly Leu Glu Trp Val
            35                  40                  45

Ala Ser Ile Tyr Pro Tyr Ser Gly Ser Thr Tyr Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Tyr Gly Tyr Ala Met Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
        210                 215                 220

Thr Cys His His His His His His
225                 230

<210> SEQ ID NO 81
```

```
<211> LENGTH: 227
<212> TYPE: PRT
<213> ORGANISM: Artificial Sequence
<220> FEATURE:
<223> OTHER INFORMATION: light chain of Fab 2D2

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Tyr Trp Val Ser
                85                  90                  95

Pro Phe Thr Phe Gly Gln Gly Thr Lys Val Glu Ile Lys Arg Thr Val
            100                 105                 110

Ala Ala Pro Ser Val Phe Ile Phe Pro Pro Ser Asp Ser Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Gly Gly Ser Asp Tyr Lys Asp Asp
    210                 215                 220

Asp Asp Lys
225

<210> SEQ ID NO 82
<211> LENGTH: 232
<212> TYPE: PRT
<213> ORGANISM: Artificial Sequence
<220> FEATURE:
<223> OTHER INFORMATION: heavy chain of Fab 2D5

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Ser
            20                  25                  30

Ser Ile His Trp Val Arg Gln Ala Pro Gly Lys Gly Leu Glu Trp Val
        35                  40                  45

Ala Ser Ile Ser Pro Tyr Tyr Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
```

```
                    85                  90                  95
Ala Arg Ser His Phe Gly Ala Leu Asp Tyr Trp Gly Gln Gly Thr Leu
                100                 105                 110

Val Thr Val Ser Ser Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Asp Lys Thr His
        210                 215                 220

Thr Cys His His His His His His
225                 230

<210> SEQ ID NO 83
<211> LENGTH: 228
<212> TYPE: PRT
<213> ORGANISM: Artificial Sequence
<220> FEATURE:
<223> OTHER INFORMATION: light chain of Fab 2D5
<220> FEATURE:
<221> NAME/KEY: MISC_FEATURE
<222> LOCATION: (202)..(202)
<223> OTHER INFORMATION: Xaa can be any naturally occurring amino acid

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
                20                  25                  30

Val Ala Trp Tyr Gln Gln Lys Pro Gly Lys Ala Pro Lys Leu Leu Ile
            35                  40                  45

Tyr Ser Ala Ser Ser Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Gly Tyr Ser His Ser
                85                  90                  95

His Leu Ile Thr Phe Gly Gln Gly Thr Lys Val Glu Ile Lys Arg Thr
                100                 105                 110

Val Ala Ala Pro Ser Val Phe Ile Phe Pro Pro Ser Asp Ser Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
                180                 185                 190
```

Lys Val Tyr Ala Cys Glu Val Thr His Xaa Gly Leu Ser Ser Pro Val
            195                 200                 205

Thr Lys Ser Phe Asn Arg Gly Glu Cys Gly Gly Ser Asp Tyr Lys Asp
    210                 215                 220

Asp Asp Asp Lys
225

<210> SEQ ID NO 84
<211> LENGTH: 234
<212> TYPE: PRT
<213> ORGANISM: Artificial Sequence
<220> FEATURE:
<223> OTHER INFORMATION: heavy chain of Fab 2D9

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Tyr
            20                  25                  30

Ser Met His Trp Val Arg Gln Ala Pro Gly Lys Gly Leu Glu Trp Val
        35                  40                  45

Ala Ser Ile Ser Pro Ser Tyr Gly Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Tyr Tyr Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys His His His His His His
225                 230

<210> SEQ ID NO 85
<211> LENGTH: 225
<212> TYPE: PRT
<213> ORGANISM: Artificial Sequence
<220> FEATURE:
<223> OTHER INFORMATION: light chain of Fab 2D9

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45
Tyr Ser Ala Ser Ser Leu Tyr Ser Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln Trp Ser His Tyr Leu Ile
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Ser Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys Gly Gly Ser Asp Tyr Lys Asp Asp Asp
    210                 215                 220
Lys
225

<210> SEQ ID NO 86
<211> LENGTH: 753
<212> TYPE: DNA
<213> ORGANISM: Artificial Sequence
<220> FEATURE:
<223> OTHER INFORMATION: single chain variable fragment open reading
      frame for Fab 3E8

<400> SEQUENCE: 86
ggatccgaca tccagatgac ccagtcccca agctccctga gcgcatccgt gggcgatagg      60
gtgaccatca catgcagggc atctcagagc gtgtctagcg cagtggcatg gtaccagcag     120
aagccaggca aggcccctaa gctgctgatc tacagcgcct cctctctgta ttccggagtg     180
ccttctcggt tctccggcag ccggagcgga accgacttta ccctgacaat cagctccctg     240
cagccagagg atttcgccac atactattgc cagcagtcta gctactccct gatcaccttt     300
ggccagggca aaggtggaga tcaaggagga ggcagcgagg aggctccgga ggcggc         360 tctgaggtgc agctggtgga gagcggagga ggactggtgc agcctggagg cagcctgagg     420
ctgtcctgtg cagcatctgg cttcaacctg tcttactata gcatgcactg ggtgcgccag     480
gcaccaggca agggcctgga gtgggtggcc tccatctctc cctactatgg ctacacctac     540
tatgccgact ctgtgaaggg ccggttcaca atcagcgccg atacctccaa gaacacagcc     600
tatctgcaga tgaatagcct gagggcagag gacaccgcag tgtactattg cccagaggc     660 ggcgcctact attttggcta ctatggcagc ggctcctacg ccatggatta ttggggccag     720 ggcacccctgg tgacagtgtc ctcttaatct aga                                 753

<210> SEQ ID NO 87

<211> LENGTH: 717
<212> TYPE: DNA
<213> ORGANISM: Artificial Sequence
<220> FEATURE:
<223> OTHER INFORMATION: single chain variable fragment open reading frame for Fab 3G11

<400> SEQUENCE: 87

```
ggatccgaca tccagatgac ccagagccca agctccctga gcgcatccgt gggcgatagg      60
gtgaccatca catgcagggc atctcagagc gtgtctagcg cagtggcatg gtaccagcag     120
aagccaggca aggcccctaa gctgctgatc tactccgcct cctctctgta tagcggcgtg     180
ccttcccggt tctccggcag ccggagcgga accgacttta ccctgacaat cagctccctg     240
cagcctgagg atttcgccac atactattgc cagcagtgga gcttcggccc aatcaccttt     300
ggccagggca caaggtgga gatcaaggga ggaggctctg gaggaggcag cggaggcggc     360
tccgaggtgc agctggtgga gtccggcggc ggcctggtgc agccaggagg ctctctgagg     420
ctgagctgtg ccgcctccgg cttcaacatc tcctactatt ctatgcactg ggtgcgccag     480
gcaccaggca agggcctgga gtgggtggcc tccatctacc ctattctag ctccacctac     540
tatgccgact ctgtgaaggg ccggtttaca atctctgccg ataccagcaa gaacacagcc     600
tacctgcaga tgaatagcct gagggcagag gacaccgcag tgtactattg tgccagatct     660
agcgccatgg attattgggg ccagggcacc ctggtgacag tgtcctctta atctaga      717
```

<210> SEQ ID NO 88
<211> LENGTH: 714
<212> TYPE: DNA
<213> ORGANISM: Artificial Sequence
<220> FEATURE:
<223> OTHER INFORMATION: single chain variable fragment open reading frame for Fab 3H1

<400> SEQUENCE: 88

```
ggatccgaca tccagatgac ccagagccca agctccctga gcgcatccgt gggcgatagg      60
gtgaccatca catgcagggc atctcagagc gtgtctagcg cagtggcatg gtaccagcag     120
aagccaggca aggcccctaa gctgctgatc tacagcgcct cctctctgta ttccggagtg     180
ccttctcggt tctccggcag ccggagcgga accgacttta ccctgacaat cagctccctg     240
cagccagagg atttcgccac atactattgc cagcagcact cctacccat caccttggc     300
cagggcacaa aggtggagat caagggagga ggcagcggag gaggctccgg aggcggctct     360
gaggtgcagc tggtggagtc cggaggagga ctggtgcagc tggaggcag cctgaggctg     420
tcctgtgcag catctggctt caacatctct tactctagca tccactgggt gcgccaggca     480
ccaggcaagg gcctggagtg gtggcctct atctactcct attctggcag cacctactat     540
gccgacagcg tgaagggccg gtttacaatc agcgccgata cctccaagaa cacagcctat     600
ctgcagatga attccctgag ggcagaggac accgcagtgt actattgtgc cagatacggc     660
gccatggatt attggggcca gggcaccctg gtgacagtgt cctcttaatc taga      714
```

<210> SEQ ID NO 89
<211> LENGTH: 683
<212> TYPE: DNA
<213> ORGANISM: Artificial Sequence
<220> FEATURE:
<223> OTHER INFORMATION: single chain variable fragment open reading frame for Fab 2B1

<400> SEQUENCE: 89

-continued

```
catgcagggc atctcagagc gtgtctagcg cagtggcatg gtaccagcag aagccaggca    60
aggcccctaa gctgctgatc tacagcgcct cctctctgta tagcggcgtg ccatcccggt   120
tctccggcag ccggagcgga accgacttta ccctgacaat cagctccctg cagcccgagg   180
atttcgccac atactattgc cagcagtact ccggctctgg ccactatctg atcacctttg   240
gccagggcac aaaggtggag atcaagggag gaggctctgg aggaggcagc ggaggcggct   300
ccgaggtgca gctggtggag tccggcgcg gcctggtgca gcctggaggc tctctgaggc    360
tgagctgtgc agcatccggc ttcaacatct actctagctc catgcactgg gtcgccagg    420 caccaggcaa gggcctggag tgggtggcca gcatctctag ctcctctagc tacacctctt   480
atgccgacag cgtgaagggc cggtttacaa tctccgccga tacctctaag aacacagcct   540
atctgcagat gaattccctg agggcagagg acaccgcagt gtactattgt gccagaggct   600
actggtacta ttgggcctgg tgggccagcc catggatta ttggggccag ggcaccctgg    660
tgacagtgtc ctcttaatct aga                                           683
```

<210> SEQ ID NO 90
<211> LENGTH: 729
<212> TYPE: DNA
<213> ORGANISM: Artificial Sequence
<220> FEATURE:
<223> OTHER INFORMATION: single chain variable fragment open reading
      frame for Fab 2D9

<400> SEQUENCE: 90

```
ggatccgaca tccagatgac ccagagccca agctccctga gcgcatccgt gggcgatagg    60
gtgaccatca catgcagggc atctcagagc gtgtctagcg cagtggcatg gtaccagcag   120
aagccaggca aggcccctaa gctgctgatc tacagcgcct cctctctgta ttccggagtg   180
ccttctcggt tctccggcag ccggagcgga accgacttta ccctgacaat cagctccctg   240
cagccagagg atttcgccac atactattgc cagcagtggt cccactatct gatcaccttt   300
ggccagggca caaggtgga gatcaaggga ggaggcagcg gaggaggctc cggaggcggc    360
tctgaggtgc agctggtgga gtccggagga ggactggtgc agcctggagg cagcctgagg   420
ctgtcctgtg cagcatctgg cttcaacctg tactattact ctatgcactg ggtgcgccag   480
gcaccaggca agggcctgga gtgggtggcc tccatctctc ccagctacgg ctataccagc   540
tacgccgact ccgtgaaggg ccggttcaca atctctgccg ataccagcaa gaacacagcc   600
tatctgcaga tgaattccct gcgggccgag gacaccgccg tgtattactg tgccagatct   660 agctttatt actatgccct ggattactgg ggccagggaa ccctggtgac agtgtcctct    720
taatctaga                                                           729
```